(12) United States Patent
Becker et al.

(10) Patent No.: US 9,305,756 B2
(45) Date of Patent: Apr. 5, 2016

(54) PREPARATION ENHANCEMENTS AND METHODS OF USE FOR MALDI MASS SPECTROMETRY

(71) Applicant: AGENA BIOSCIENCE, INC, San Diego, CA (US)

(72) Inventors: Thomas Becker, La Jolla, CA (US); Stefan Berkenkamp, San Diego, CA (US)

(73) Assignee: Agena Bioscience, Inc., San Diego, CA (US)

( * ) Notice: Subject to any disclaimer, the term of this patent is extended or adjusted under 35 U.S.C. 154(b) by 0 days.

(21) Appl. No.: 13/801,526

(22) Filed: Mar. 13, 2013

(65) Prior Publication Data

US 2014/0260700 A1 Sep. 18, 2014

(51) Int. Cl.
*G01N 24/00* (2006.01)
*H01J 49/04* (2006.01)
*H01J 49/16* (2006.01)

(52) U.S. Cl.
CPC ........... *H01J 49/0418* (2013.01); *H01J 49/164* (2013.01)

(58) Field of Classification Search
None
See application file for complete search history.

(56) References Cited

U.S. PATENT DOCUMENTS

| | | | |
|---|---|---|---|
| 5,506,348 A | 4/1996 | Pieles | |
| 5,786,146 A | 7/1998 | Herman et al. | |
| 6,468,748 B1 | 10/2002 | Monforte et al. | |
| 6,723,564 B2 | 4/2004 | Hillenkamp | |
| 7,888,127 B2 | 2/2011 | Becker | |
| 2001/0055811 A1 | 12/2001 | Hillenkamp | |
| 2002/0048770 A1 | 4/2002 | Morozov et al. | |
| 2002/0142483 A1 | 10/2002 | Yao et al. | |
| 2003/0082600 A1 | 5/2003 | Olek et al. | |
| 2003/0180779 A1 | 9/2003 | Lofton-Day et al. | |
| 2005/0074759 A1 | 4/2005 | Petersson et al. | |
| 2005/0112590 A1 | 5/2005 | Boom | |
| 2005/0178959 A1 | 8/2005 | Lopez-Avila et al. | |
| 2006/0023808 A1 | 2/2006 | Hajivandi et al. | |
| 2006/0094065 A1 | 5/2006 | Lopez-Avila | |
| 2006/0106108 A1 | 5/2006 | Kammeijer et al. | |
| 2006/0110833 A1 | 5/2006 | Agnes et al. | |

(Continued)

FOREIGN PATENT DOCUMENTS

EP  1 284 495  2/2003
EP  1 830 184  9/2007

(Continued)

OTHER PUBLICATIONS

Yan, H. et al., Noncovalent antibody immobilization on porous silicon combined with miniaturized solid-phase extraction (SPE) for array based immunoMALDI assay, 2011, Analytical Chemistry, vol. 83, pp. 4942-4948.*

(Continued)

*Primary Examiner* — Robert Xu
(74) *Attorney, Agent, or Firm* — Grant IP, Inc.

(57) ABSTRACT

Provided herein are compositions and methods useful for preparing and analyzing a sample on a substrate by matrix assisted laser desorption ionization (MALDI) mass spectrometry (MS). In some embodiments, compositions provided herein comprise a substrate, matrix and nanoparticles, and sometimes comprise one or more additives and sometimes an analyte. Compositions provided herein sometimes comprise nanoparticles that include or are made up of silicon dioxide.

19 Claims, 2 Drawing Sheets

(56) References Cited

U.S. PATENT DOCUMENTS

| | | | |
|---|---|---|---|
| 2006/0183128 | A1 | 8/2006 | Berlin et al. |
| 2006/0214104 | A1 | 9/2006 | Pope et al. |
| 2006/0255256 | A1 | 11/2006 | Hayden et al. |
| 2007/0298006 | A1 | 12/2007 | Tomalia et al. |
| 2009/0026082 | A1 | 1/2009 | Rothberg et al. |
| 2009/0029377 | A1 | 1/2009 | Lo et al. |
| 2009/0181376 | A1 | 7/2009 | Becker |
| 2009/0215709 | A1 | 8/2009 | Van Criekinge et al. |
| 2009/0317818 | A1 | 12/2009 | Ehrich et al. |
| 2010/0105049 | A1 | 4/2010 | Ehrich et al. |
| 2010/0167940 | A1 | 7/2010 | Feinberg |
| 2011/0028333 | A1 | 2/2011 | Christensen et al. |
| 2012/0104243 | A1 | 5/2012 | Verbeck, IV et al. |
| 2013/0034546 | A1 | 2/2013 | Rava et al. |

FOREIGN PATENT DOCUMENTS

| | | | | |
|---|---|---|---|---|
| EP | 2416345 A1 | * | 2/2012 | ............ H01J 49/04 |
| JP | 06-322274 | | 11/1994 | |
| JP | 2005-114515 | | 4/2005 | |
| JP | 2005-221250 | | 8/2005 | |
| JP | 2007-516448 | | 6/2007 | |
| JP | 2007-309860 | | 11/2007 | |
| WO | WO 97/27325 | | 7/1997 | |
| WO | WO 99/05319 | | 2/1999 | |
| WO | WO 2005/064330 | | 7/2005 | |
| WO | WO 2005/065307 | | 7/2005 | |
| WO | WO 2006/056480 | | 6/2006 | |
| WO | WO 2006/083151 | | 8/2006 | |
| WO | WO 2007/061643 | | 5/2007 | |
| WO | WO 2007/066227 | | 6/2007 | |
| WO | WO 2007/140417 | | 12/2007 | |
| WO | WO 2007/147063 | | 12/2007 | |
| WO | WO 2009/032779 | | 3/2009 | |
| WO | WO 2009/032781 | | 3/2009 | |
| WO | WO 2009/046445 | | 4/2009 | |
| WO | WO 2009/052837 | * | 4/2009 | ............ G01N 33/68 |
| WO | WO 2009/091841 | | 7/2009 | |
| WO | WO 2010/004265 | | 1/2010 | |
| WO | WO 2010/033639 | | 3/2010 | |
| WO | WO 2010/115016 | | 10/2010 | |
| WO | WO 2011/034631 | | 3/2011 | |
| WO | WO 2011/143659 | | 11/2011 | |
| WO | WO 2012/149339 | | 11/2012 | |

OTHER PUBLICATIONS

Carda-Broch et al., "Ionic matrices for matrix-assisted laser desorption / ionization time-of-flight detection of DNA oligomers," Rapid Commun. Mass Spectrom. 2003; 17: 553-560.
Garcia et al., "Improvement of the MALDI-TOF Analysis of DNA with Thin-Layer Matrix Preparation," Anal. Chem. 2002, 74, 2083-2091.
Ho et al., "Nanoparticle-assisted MALDI-TOF MS combined with seed-layer surface preparation for quantification of small molecules," Analytica Chimica Acta, 697(2011) 1-7.
Hua et al., "Silver nanoparticles as matrix for laser desorption/ ionization mass spectrometry of peptides," J Nanopart Res (2007) 9:1133-1138.
Kim et al., "Improving Spot Homogeneity by Using Polymer Substrates in Matrix-Assisted Laser Desorption/Ionization Mass Spectrometry of Oligonucleotides" (Anal. Chem. 2001, 73, 2617-2624).
Soltwisch et al., "A binary matrix of 2,5-dihydroxybenzoic acid and glycerol produces homogenous sample preparations for matrix-assisted laser desorption/ionization mass spectrometry," Rapid Commun. Mass Spectrom. 2008; 22: 59-66.
Tseng et al., "Dihydrobenzoic Acid Modified Nanoparticle as a MALDI-TOF MS Matrix for Soft Ionization and Structure Determination of Small Molecules with Diverse Structures," J Am Soc Mass Spectrom 2010, 21, 1930-1939.
Vanderpuije et al., "Mixed Monolayer-Protected Gold Nanoclusters as Selective Peptide Extraction Agents for MALDI-MS Analysis" Anal. Chem. 2006. 78, 5491-5496.
Wu et al., "Gold Nanoparticles as Assisted Matrices for the Detection of Biomolecules in a High-Salt Solution through Laser Desorption/ Ionization Mass Spectrometry" J Am Soc Mass Spectrom 2009, 20, 875-882.
Gao et al., "MALDI mass spectrometry for nucleic acid analysis" Topics in Current Chemistry (2013)331:55-77.
Partial International Search Report mailed on Oct. 29, 2014 in International application No. PCT/US2014/020001, filed on Mar. 3, 2014 and Published as WO 2014/164026 on Oct. 9, 2014.
Akirav et al., "Detection of β cell death in diabetes using differentially methylated circulating DNA" PNAS USA (2011) 108:19018-19023.
Asara and Alison, "Enhanced Detection of Oligonucleotides in UV MALDI MS Using the Tetraamine Spermine as a Matrix Additive," Anal Chem. (1999) 71:2866-2870.
Ayorinde FO, Bezabeh DZ, Delves IG., "Preliminary investigation of the simultaneous detection of sugars, ascorbic acid, citric acid, and sodium benzoate in non-alcoholic beverages by matrix-assisted laser desorption/ionization time-of-flight mass spectrometry" Rapid Commun Mass Spectrom. (2003) 17(15):1735-42.
Battagli et al., "Promoter Hypermethylation of Tumor Suppressor Genes in Urine from Kidney Cancer Patients" Cancer Research (2003) 63:8695-8699.
Beaucage and Caruthers, "Deoxynucleoside Phosphoramidites—A New Class of Key Intermediates for Deoxypolynucleotide Synthesis," (1981) Tetrahedron Letts. 22:1859-1862.
Cantu et al., Anal Chem. vol. 72, pp. 5820-5828, published on the web 26, Oct. 2000.
Chen and Chen, "Reducing the Alkali Cation Adductions of Oligonucleotides Using Sol-Gel-Assisted Laser Desorption/Ionization Mass Spectometry," Anal. Chem. (2003) 75:4223-4228.
Chen et al., "Methylation Target Array for Rapid Analysis of CpG Island Hypermethylation in Multiple Tissue Genomes" American Journal of Pathology (2003) 163:37-45.
Current Protocols in Molecular Biology, John Wiley & Sons, N.Y., 6.3.1-6.3.6 (1989).
Djoman et al., "RNA-ascorbate interaction," Journal of Biomolecular Structure and Dynamics, Jun. 1998, vol. 15, No. 6, pp. 1115-1120.
Ehrlich, "DNA methylation in cancer: too much, but also too little" Oncogene (2002) 21:5400-5413.
Electrospray Ionization Mass Spectrometry: Fundamentals, Instrumentation and Applications edited by Cole (John Wiley and Sons, New York) 1997.
Extended European Search report dated: Jan. 11, 2011, in European Application No. EP09702741.
Harris et al., "Single-Molecule DNA Sequencing of a Viral Genome," Science 320:106-109 (2008).
Husseiny et al., "Development of a Quantitative Methylation-Specific Polymerase Chain Reaction Method for Monitoring Beta Cell Death in Type 1 Diabetes" PLOS One (2012) 7(10):e47942.
International Preliminary Report on Patentability, mailed on: Jul. 29, 2010 for International application No. PCT/US2009/031020 filed on Jan. 12, 2009 and published as WO 09/091841 on: Oct. 8, 2009.
International Search Report and Written Opinion, mailed on: Aug. 19, 2009 for International application No. PCT/US2009/031020 filed on Jan. 12, 2009 and published as WO 09/091841 on: Oct. 8, 2009.
Jurinke, C., Oeth, P., van den Boom, D., "MALDI-TOF mass spectrometry: a versatile tool for high-performance DNA analysis", Mol. Biotechnol. 26, 147-164 (2004).
Laugesen and Roepstroff, "Combination of Two Matrices Results in Improved Performance of MALDI MS for Peptide Mass Mapping and Protein Analysis," J. Am. Soc. Mass Spectrom. (2003) 14:992-1002.
Li et al. "Evaluation of ammonium salts as co-matrices for matrix-assisted laser desorption/ionization mass spectrometry of oligonucleotides" Rapid Comm. Mass Spectrom. 12:993-998 (1998).
M.C. Fitzgerald and L.M. Smith, Annu. Rev. Biophys. Biomol. Struc. (1995) 24:117-140.
Margulies et al., "Genome sequencing in microfabricated high-density picolitre reactors," Nature 437:376-380 (2005).
Metzker, "Sequencing technologies—the next generation," Nature Rev 11:31-46 (2010).

(56) References Cited

OTHER PUBLICATIONS

Moudrianakis et al., "Base Sequence Determination in Nucleic Acids with the Electron Microscope, III. Chemistry and Microscopy of Guaninie-Labeled DNA," Proc Natl Acad Sci USA. Mar. 1965; 53:564-71.
Neault et al., "DNA-drug interaction. The effects of vitamin C on the solution structure of calf thymus DNA studied by FTIR and laser Raman difference spectroscopy," Journal of Biomolecular Structure and Dynamics, 1995, vol. 13, No. 2, pp. 387-397.
Needham-VanDevanter et al. "Characterization of an adduct between CC-1065 and defined oligodeoxynucleotide," (1984) Nucleic Acids Res. 12:6159-6168.
Nishiyama et al., "A DNA Repeat, NBL2, Is Hypermethylated in Some Cancers but Hypomethylated in Others" Cancer Biology & Therapy (2005) 4:440-448.
Nordhoff et al., "Mass spectrometry of nucleic acids" Mass Spectrometry Reviews, 1996, 15, 67-138.
Nordhoff, E., et al., "Matrix-assisted Laser Desorption/Ionization Mass Spectrometry of Nucleic Acids with Wavelengths in the Ultraviolet and Infrared" Rapid Comm. Mass Spectrom. 1992, 6, 771-776.
O'Brien BA at al. Mass Spectrometric Screening for Polyphenolic Protein Adducts. Proceedings of the 50th ASMS Conference on Mass Spectrometry and Allied Topics, Orlando, Florida, Jun. 2-6, 2002. pp. 409-410.
Oeth, P. et al., "iPLEX™ Assay: Increased Plexing Efficiency and Flexibility for MassARRAY® System through single base primer extension with mass-modified Terminators" Sequenom Application Note (2005).
Pearson and Regnier "High-Performance Anion-Exchange Chromatography of Oligonucleotides," (1983) J. Chrom. 255:137-149.
Pieles, et al., "Matrix-assisted laser desorption ionization time-of-flight mass spectrometry: a powerful tool for the mass and sequence analysis of natural and modified oligonucleotides," Nucleic Acid Research, 1993, 21:14, 3191-3196.
Rathi et al., "Aberrant Methylation of the H1C1 Promoter Is a Frequent Event in Specific Pediatric Neoplasms" Clinical Cancer Research (2003) 9:3674-3578.
Shahgoli et al, "Sugar additives for MALDI matrices improve signal allowing the smallest nucleotide change (A:T) in a DNA sequence to be resolved," Nucleic Acids Research 2001, 21:19, e91 1-10.
Ushijima, "Detection and interpretation of altered methylation patterns in cancer cells" Nature Reviews (2005) 5: 223-231.
Vaickus, "Immune markers in hematologic malignancies," Crit. Rev. in Oncol./Hemotol. 11:267-297 (1991).

Volkerding et al. "Next-generation sequencing: from basic research to diagnostics," Clin Chem 55:641-658 (2009).
Wu et al., Anal Chem, vol. 75, pp. 4827-4832, published on the web Aug. 16, 2003.
Wu, J.K., et al., "Matrix-assisted Laser Desorption Time-of-flight Mass Spectrometry of Oligonucleotides Using 3-Hydroxypicolinic Acid as an Ultraviolet-sensitive Matrix," Rapid Comm. Mass Spectrom. 1993, 7:142-146.
Zenobi et al., "Ion Formation in MALDI Mass Spectrometry," Mass Spectrometry Reviews. 1998, 17, 341.
Zhou et al., "A mixed matrix of 3-hydroxypicolinic acid and pyrazinercarboxylic acid for matrix-assisted laser desorption/ionization time-of-flight mass spectrometry of oligodeoxynucleotides," Rapid Communications in Mass Spectrometry, 2003:18:787-794.
Zhu YF et al., "The effect of ammonium salt and matrix in the detection of DNA by matrix-assisted laser desorption/ionization time-of-flight mass spectrometry" Rapid Commun Mass Spectrom. (1996) 10:1591-96.
Office Action dated: Dec. 2, 2008 in U.S. Appl. No. 12/014,671, filed Jan. 15, 2008, published as: US2009/0181376 on Jul. 16, 2009 and issued as: U.S. Pat. No. 7,888,127 on Feb. 15, 2011.
Office Action dated: Mar. 26, 2010 in U.S. Appl. No. 12/014,671, filed Jan. 15, 2008, published as: US2009/0181376 on Jul. 16, 2009 and issued as: U.S. Pat. No. 7,888,127 on Feb. 15, 2011.
Office Action dated: Oct. 6, 2010 in U.S. Appl. No. 12/014,671, filed Jan. 15, 2008, published as: US2009/0181376 on Jul. 16, 2009 and issued as: U.S. Pat. No. 7,888,127 on Feb. 15, 2011.
Office Action dated: Apr. 8, 2013 in U.S. Appl. No. 12/986,975, filed, Jan. 7, 2011, published as: US2011/0172124 on Jul. 14, 2011.
Office Action dated: Oct. 28, 2013 in U.S. Appl. No. 12/986,975, filed Jan. 7, 2011, published as: US2011/0172124 on Jul. 14, 2011.
Office Action dated Dec. 19, 2013 in Japanese Patent Application No. 2013-95670, published as JP 2013-148596 on Aug. 1, 2013.
International Search Report and Written Opinion mailed on Dec. 16, 2014 in International application No. PCT/US2014/020001, filed on Mar. 3, 2014 and Published as WO 2014/164026 on Oct. 9, 2014.
Office Action dated Jun. 11, 2015 in U.S. Appl. No. 12/986,975, filed Jan. 7, 2011 and published as US 2011/0172124 on Jul. 14, 2011.
International Preliminary Report on Patentability mailed on Sep. 24, 2015 in International application No. PCT/US2014/020001, filed on Mar. 3, 2014 and Published as WO 2014/164026 on Oct. 9, 2014.
Office Action dated Dec. 4, 2015 in U.S. Appl. No. 12/986,975, filed Jan. 7, 2011 and published as US 2011/0172124 on Jul. 14, 2011.

* cited by examiner

PREPARATION ENHANCEMENTS AND METHODS OF USE FOR MALDI MASS SPECTROMETRY

FIELD

The technology relates to matrix assisted laser desorption ionization (MALDI) mass spectrometry.

DESCRIPTION

Mass spectrometry can be utilized to analyze molecular analytes such as peptides, proteins, polymers, DNA, RNA, intact bacteria or cells, carbohydrates, sugars and other molecules. Multiple mass spectrometry formats are available and can be employed. In a particular type of mass spectrometry format, matrix assisted laser desorption ionization (MALDI) is utilized to volatilize and ionize analyte. MALDI mass spectrometry generally involves the use of a matrix material that typically is in crystalline form prior to volatilization and ionization of an analyte for mass spectrometry analysis. MALDI mass spectrometry often involves use of a time of flight (TOF) mass spectrometer, which can detect ions at different times after they travel through the spectrometer.

Provided herein are compositions and substrates useful for matrix assisted laser desorption ionization (MALDI) mass spectrometry (MS).

Provided in certain aspects are compositions comprising nanoparticles (e.g., liquid compositions). Without being limited by theory, nanoparticles in a liquid composition comprising a MALDI matrix can enhance matrix crystal homogeneity in part by providing relatively uniform seeding surfaces for matrix crystallization. A composition comprising a MALDI matrix sometimes is a liquid solution comprising nanoparticles, and sometimes the liquid solution is spotted as a sample on a substrate and present as a spot at a particular domain. Any matrix suitable for conducting MALDI MS may be included in a composition comprising nanoparticles, and one or more types of matrix and one or more types of nanoparticles may be included. A matrix included in a composition sometimes is a hydrophobic MALDI matrix. A composition comprising nanoparticles and a MALDI matrix sometimes does not include an analyte and sometimes includes one or more analytes. A composition comprising nanoparticles and a MALDI matrix sometimes comprises one or more additives. Any suitable additive may be included in a composition, and sometimes a composition includes a free-radical scavenger (e.g., ascorbic acid), oxalate (e.g., ammonium oxalate), or combination thereof.

Also provided in certain aspects are substrates comprising structural topologies on or in a substrate configured to isolate a sample to a particular domain of the substrate. Without being limited by theory, such topology can isolate a sample to a particular domain on the substrate as the sample dries. As a sample dries it sometimes shifts from substantially liquid form to substantially crystalline form. Surface topology can anchor a sample at one or more domains on a substrate, which domains often are arranged as equidistant locations in an array on the substrate. Surface topology described herein can enhance MS data acquisition for samples by defining the location of the samples on a substrate. Surface topology described herein also can enhance crystallization uniformity of samples on a MS substrate and further enhance MALDI-TOF MS data by reducing ion time of flight variability, as described in greater detail hereafter.

A mass spectrometry substrate sometimes comprises a substantially planar surface and topology features, each of which topology features is configured to retain a sample deposited at a domain on the substrate. A sample can contain an analyte, nanoparticles, matrix, additive, the like and combinations thereof. Each domain on a substrate can comprise one or more topology features, each of which topology features also is referred to herein as a containment structure. Any type of containment structure, or combination of containment structures, configured to isolate a sample may be present at a domain on a substrate. A containment structure sometimes is a structural obstacle that interferes with movement of a sample on the substrate (e.g., a depression or projection on a flat or substantially flat substrate). A containment structure sometimes functions as an obstacle that that interferes with movement of a sample via chemical interaction, surface energy interaction, surface texture interaction, the like or combination thereof.

Provided also in certain aspects are combinations of a substrate, comprising a surface topology described herein, and a sample or spot that includes nanoparticles and a MALDI matrix. A sample or spot that includes nanoparticles and a MALDI matrix sometimes includes an analyte and sometimes includes no analyte.

Also provided in certain aspects are methods for analyzing an analyte by MALDI MS using a substrate that includes a surface topology feature described herein and/or a composition comprising nanoparticles and a MALDI matrix. Any analyte that can be analyzed by MALDI MS analysis can be assessed. Non-limiting examples of analytes include nucleotides, oligonucleotides, polynucleotides, nucleic acid, peptides, proteins, polymers (e.g., synthetic polymer, industrial polymer, plastic polymer), saccharides, polysaccharides, sugars, carbohydrates, lectins, lipids, glycoproteins, lipoproteins, small molecules, small chemical entities, metabolites, natural products, pharmaceuticals, conjugates, the like and combinations thereof. Non-limiting examples of nucleic acid include deoxyribonucleic acid (DNA), ribonucleic acid (RNA), protein nucleic acid (PNA), single-stranded nucleic acid, double-stranded nucleic acid and the like. A nucleic acid analyte sometimes has a nominal, average or mean length of about 5 to about 10,000 base pairs, about 100 to about 1,000 base pairs, about 100 to about 500 base pairs, or about 10, 15, 20, 25, 30, 35, 40, 45, 50, 55, 60, 65, 70, 75, 80, 85, 90, 95, 100, 200, 300, 400, 500, 600, 700, 800, 900, 1000, 2000, 3000, 4000, 5000, 6000, 7000, 8000 or 9000 base pairs.

These aspects and further aspects and embodiments are described in greater detail hereafter.

Compositions Comprising Nanoparticles and Matrix

A composition comprising nanoparticles and a matrix (nanoparticle/matrix composition) can be provided and used in various forms. A nanoparticle/matrix composition sometimes is provided in solid form, crystalline form, liquid form, the like and combinations thereof. A sample sometimes comprises an analyte, matrix composition (e.g., nanoparticle/matrix composition) or combination thereof. A matrix composition typically includes a MALDI MS matrix, often comprises nanoparticles, and sometimes comprises one or more additives.

A nanoparticle/matrix composition sometimes is utilized as a reagent to prepare a sample for MS analysis. A nanoparticle/matrix composition sometimes is provided in liquid form or solid form (e.g., crystalline form) and a user can utilize the composition to prepare a substrate for MS analysis. In a non-limiting example, a user may mix an analyte with a nanoparticle/matrix composition in liquid or solid form, and then deposit the mixture onto one or more domains of a MS substrate in preparation for MS analysis. One or both of the analyte composition and nanoparticle/matrix composition generally are in liquid form when they are mixed. In another non-limiting example, a user may deposit a nanoparticle/matrix composition in liquid form onto one or more domains of a MS substrate and expose the substrate to conditions under which the matrix in the composition crystallizes. A user then may deposit analyte onto one or more domains of such a substrate containing the nanoparticle/matrix composition. Domains on a substrate sometimes include the same composition or different compositions, and a subset of domains on a substrate sometimes include different compositions (e.g., different amount of one or more sample components, different sample components (e.g., different analytes). A nanoparticle/matrix composition described herein sometimes includes components other than nanoparticles and matrix, and sometimes includes an additive, analyte the like or combination thereof. A nanoparticle/matrix composition can be present in a fluid handling container (e.g., tube), in a fluid dispensing device (e.g., manual or automated dispenser), and/or at one or more domains of a substrate.

A MALDI MS substrate comprising a nanoparticle/matrix composition sometimes is provided, and the nanoparticle/matrix composition sometimes is present in crystalline form at one or more domains of the substrate. A user utilizing such a substrate can deposit an analyte at one or more domains containing the nanoparticle/matrix composition, and utilize the resulting substrate for MALDI MS analysis. In such instances, deposition of analyte often dissolves crystalline matrix at a domain on the substrate to which the analyte is applied, and the sample typically then is recrystallized. Accordingly, crystals on a substrate typically include matrix and nanoparticles and sometimes include analyte. Thus, a user may deposit analyte at one or more domains of a substrate comprising matrix and nanoparticles in substantially crystalline form, and the resulting sample can re-crystallize (e.g., the matrix and analyte may co-crystallize).

In addition to surface topology, nanoparticles can enhance matrix crystal homogeneity and enhance MALDI-TOF MS analysis. Matrix crystal heterogeneity (e.g., unevenness in crystal topology) can negatively affect MALDI MS spectra. Increased uniformity of distribution in the thickness of crystalline matrix (i.e., z-direction) at a domain can result in less variability in flight time, often resulting in higher quality (e.g., higher resolution) MALDI-TOF mass spectra. Without being limited by theory, nanoparticles can enhance matrix crystal homogeneity by providing regular and multiple crystal seeding surfaces.

Nanoparticles sometimes independently have an average, mean, median, nominal, minimum or maximum diameter of about 1 nanometer (nm) to about 100 nm, of about 5 nm to about 30 nm, of about 10 nm to about 20 nm (e.g., about 10, 11, 12, 13, 14, 15, 16, 17, 18, 19 or about 20 nm) or about 15 nm. Where a composition includes two or more different types of nanoparticles (e.g., 2, 3, 4, 5, 6, 7, 8, 9, 10 types of nanoparticles), the average, mean, median, nominal, minimum or maximum diameter of each type of nanoparticle may be the same or different.

A nanoparticle sometimes consists of, consists essentially of, or comprises one or more metalloids, non-limiting examples of which include boron and silicon, the like and combinations thereof. A nanoparticle that "consists essentially of" a metalloid can contain one or more non-metalloid contaminants present at non-detectable levels or at relatively low levels (e.g., about 10%, 5%, 1%, 0.1% 0.01%, 0.001%, 0.0001%, 0.00001% or less of the amount of the metalloid, e.g., about 1 ppm, 0.1 ppm, 0.01 ppm, 0.001 ppm, 0.0001 ppm, 0.00001 ppm or less of the metalloid). A nanoparticle sometimes consists of, consists essentially of or comprises silicon (e.g., silicon dioxide (i.e., $SiO_2$)). Nanoparticles sometimes consist of or consist essentially of fumed silica particles.

A nanoparticle sometimes is a metal (i.e., consists of one or more metals), consists essentially of one or more metals or comprises one or more metals. Non-limiting examples of metals include iron, gold, silver, platinum, aluminum, titanium, tantalum, vanadium, the like and combinations thereof. A nanoparticle that "consists essentially of" a metal can contain one or more non-metal contaminants present at relatively low levels (e.g., less than about 10%, 0.1% 0.01%, 0.001%, 0.0001%, or less than about 0.00001% of the amount of metal). A nanoparticle sometimes comprises, consists of or consists essentially of iron (e.g., $Fe_3O_4$), titanium dioxide (e.g., $TiO_2$), the like or combination thereof. A nanoparticle sometimes comprises no metal or substantially no metal. A nanoparticle comprising substantially no metal may contain an insignificant amount of metal or no detectable amount of metal. A nanoparticle comprising substantially no metal may contain trace amounts of metal contaminants. A trace amount can be less than about 10%, 5%, 1%, 0.1% 0.01%, 0.001%, 0.0001%, 0.00001% or less. In some embodiments a trace amount is less than about 1 ppm, 0.1 ppm, 0.01 ppm, 0.001 ppm, 0.0001 ppm, 0.00001 ppm or less.

A nanoparticle sometimes is a polymer (i.e., consists of one or more polymers), consists essentially of one or more polymers or comprises one or more polymers. Non-limiting examples of polymers include polypropylene (PP), polyethylene (PE), high-density polyethylene (HDPE), low-density polyethylene (LDPE), polyethylene teraphthalate (PET), polyvinyl chloride (PVC), polytetrafluoroethylene (PTFE), polystyrene (PS), high-density polystyrene, acrylnitrile butadiene styrene copolymers, crosslinked polysiloxanes, polyurethanes, (meth)acrylate-based polymers, cellulose and cellulose derivatives, polycarbonates, ABS, tetrafluoroethylene polymers, poly(2-hydroxy ethyl methacrylate), poly(N-vinyl pyrrolidone), poly(methyl methacrylate), poly(vinyl alcohol), poly(acrylic acid), polyacrylamide, poly(ethylene-co-vinyl acetate), poly(ethylene glycol), poly(methacrylic acid), polylactides (PLA), polyglycolides (PGA), poly(lactide-co-glycolides) (PLGA), polyanhydrides, polyorthoesters, polycyanoacrylates, polycaprolactone, the like, copolymers thereof and combinations of the foregoing. A nanoparticle that "consists essentially of" a polymer can contain one or more non-polymer contaminants present at relatively low levels (e.g., less than about 10%, 0.1%0.01%, 0.001%, 0.0001%, or less than about 0.00001% of the amount of polymer). In some embodiments, a nanoparticle comprises no polymer or substantially no polymer. A nanoparticle comprising substantially no polymer may contain an insignificant amount of polymer or no detectable amount of polymer. A nanoparticle comprising substantially no polymer may contain trace amounts of polymer contaminants. A trace amount can be less than about 10%, 5%, 1%, 0.1% 0.01%, 0.001%, 0.0001%, 0.00001% or less. In some embodiments a trace amount is less than about 1 ppm, 0.1 ppm, 0.01 ppm, 0.001 ppm, 0.0001 ppm, 0.00001 ppm or less.

A nanoparticle often is inert or substantially inert, and often does not associate with or substantially associate with another molecule (e.g., analyte, matrix, additive). A substantially inert nanoparticle, or nanoparticle that does not substantially associate with another molecule, typically is largely resistant to reacting with another molecule (e.g., analyte, another nanoparticle, matrix, additive, the like or combination thereof). There sometimes is a minimal amount of interaction between a nanoparticle and another molecule and such interaction generally does not significantly interfere with generating MS signals for an analyte. For example, an interaction between a nanoparticle and another molecule typically does not generate MS signals that overlap with, significantly shift or obscure MS signals arising from an analyte. An inert or substantially inert nanoparticle material often is resistant to forming adducts to the analyte. A nanoparticle often is resistant to forming a multimer with other nanoparticles. A nanoparticle often does not form covalent bonds with another molecule. A nanoparticle sometimes forms weak to moderate non-covalent interactions with another molecule (e.g., analyte), non-limiting examples of which include van der Waals interactions, hydrogen bonding, weak ionic interactions, weak electrostatic interactions and/or hydrophilic or hydrophobic interactions. A nanoparticle often lacks, and often is not derivatized with, a functional group. A nanoparticle often does not give rise to a signal in a MALDI MS spectrum.

Nanoparticles in a composition often are not in association with a matrix, and often are not covalently linked to a matrix. Nanoparticles in a composition often are not in association with an analyte (e.g., peptide or protein), and nanoparticles often are not covalently linked to an analyte (e.g., not covalently linked to a peptide or protein). A composition often comprises substantially no component or components that react with matrix or nanoparticles, or the matrix and the nanoparticles, and covalently link the matrix to the nanoparticles.

Any suitable method may be utilized to prepare a nanoparticle/matrix composition. Nanoparticles sometimes are suspended in a suitable solvent (e.g., water), and nanoparticles sometimes are insoluble in a solvent (e.g., insoluble in water) and provided as a suspension. Nanoparticles sometimes are suspended in liquid form (e.g., water) and combined with a matrix solution. In some embodiments, nanoparticles are substantially free of impurities and therefore do not need to be purified. Sometimes nanoparticles are not substantially pure, and may be further purified by a suitable method to remove impurities, for example, by ion-exchange resin purification. In some embodiments, nanoparticles are added directly (e.g., in dry from) to a matrix solution.

Nanoparticles sometimes are added to a matrix solution to a final concentration of about 1 microgram per milliliter (ug/ml) to about 500 ug/ml. Nanoparticles sometimes are added to a matrix solution to a final concentration of about 75 ug/ml to about 300 ug/ml. Nanoparticles can be added to a matrix solution to a final concentration of about 125 ug/ml to about 250 ug/ml. Nanoparticles sometimes are added to a matrix solution to a final concentration of about 100, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295 or about 300 ug/ml. A nanoparticle/matrix solution sometimes is saturated with nanoparticles.

A composition (e.g., sample deposited on a substrate) sometimes comprises about 0.001 nanogram (ng; or about 1 picogram (pg)) to about 10,000 ng (or about 10 micrograms (ug)), about 10 pg to about 5 ug, about 20 pg to about 2.5 ug, about 1 ng to about 500 ng, or about 1 ng to about 100 ng of nanoparticles. A composition comprises about 1, 5, 10, 20, 30, 40, 50, 60, 70, 80, 90, 100, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295 or 300 ng of nanoparticles, in some embodiments. A composition comprises about 1, 5, 10, 20, 30, 40, 50, 60, 70, 80, 90, 100, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295 or 300 pg of nanoparticles, in certain embodiments. In some embodiments, a composition comprises about 1, 2, 3, 4, 5, 6, 7, 8, 9 or 10 ug of nanoparticles.

Any matrix suitable for use for MADLI MS can be utilized for preparing a nanoparticle/matrix composition. A matrix generally is an energy absorbing (e.g., IR or UV-absorbent) substance that absorbs energy from an energy source (e.g., a laser), thereby enabling desorption of an analyte from the substrate. A matrix often is selected according to the type of analyte being analyzed by MALDI MS, and sometimes a matrix suitable for analyzing nucleic acid, a matrix suitable for analyzing peptide or protein, or a matrix suitable for analyzing a polymer, is utilized. A matrix selected often is a polar matrix and sometimes is a non-polar matrix (e.g., alpha-cyano-4-hydroxycinnamic acid (alpha-CHCA)). Non-limiting examples of matrix that can be included in a nanoparticle/matrix composition include 3-hydroxypicolinic acid (3-HPA), 2,5-dihydroxybenzoic acid (DHB), alpha-cyano-4-hydroxycinnamic acid (alpha-CHCA), picolinic acid (PA), 3-aminopicolinic acid, 3-picolinic acid, 2,4,6-trihydroxyacetophenone (THAP), anthranilic acid, nicotinic acid, salicylamide, 1-isoquinolinol, T-2-(3-(4-t-Butyl-phenyl)-2-methyl-2-propenylidene) malononitrile (DCTB), sinapic acid (SA), dithranol (DIT), 3-aminoquinoline, trans-3-indoleacrylic acid (IAA), 2-(4-hydroxyphenylazo)benzoic acid (HABA), succinic acid, 2,6-dihydroxyacetophenone, ferulic acid, caffeic acid, glycerol, nitroaniline, the like or combinations thereof.

A nanoparticle/matrix composition can include one or more types of matrix (e.g., 1, 2, 3, 4, 5, 6, 7, 8, 9, 10 types of matrix). An amount of a type of matrix in a composition sometimes is optimized for the type of analyte analyzed. In certain embodiments, total concentration of matrix in a composition (e.g., solution deposited at a substrate domain) is about 1 mg/ml to about 200 mg/ml, about 1 mg/ml to about 200 mg/ml of matrix, or about 40 mg/ml to about 100 mg/ml of matrix (e.g., about 40 mg/ml, 45 mg/ml, 50 mg/ml, 55 mg/ml, 60 mg/ml, 65 mg/ml, 70 mg/ml, 75 mg/ml, 80 mg/ml, 85 mg/ml, 90 mg/ml, 95 mg/ml or 100 mg/ml of matrix). In some embodiments, total concentration of matrix in a composition is about 1 mM to about 1M (e.g., about 5, 10, 20, 30, 40, 50, 60, 70, 80, 90, 100, 150, 200, 250, 300, 350, 400, 450, 500, 550, 600, 700, 800 or 900 mM matrix).

A matrix sometimes is predominantly in a liquid or solid form in a nanoparticle/matrix composition. A matrix (e.g., in solid (e.g., crystalline) or liquid form) sometimes is dissolved and/or suspended in a suitable solvent, non-limiting examples of which include water, alcohol (e.g., methanol, propanol, ethanol), acetone, chloroform, acetonitrile, trifluoroacetic acid, the like and combinations thereof. A matrix in predominantly solid form sometimes is predominantly in a crystalline form. A crystalline form of a matrix often comprises solid and some solvent. Crystals can include matrix, nanoparticles, additive, analyte, solvent (e.g., water), the like or combinations thereof. Conditions for preparing matrix in a substantially crystalline form are known and described herein.

In some embodiments, a composition comprises a matrix and nanoparticles (e.g., before or after deposition at a domain on a substrate) at a matrix to nanoparticle ratio (e.g., mole ratio or molar concentration ratio) of about 0.1:1 to about 30,000:1, about 1:1 to about 20,000:1, about 10:1 to about 20,000:1 or about 30:1 to about 20,000:1. In some embodiments a solution or spot comprises a matrix to nanoparticle ratio (e.g., mole ratio or molar concentration ratio) of about 1000:1, 900:1, 800:1, 700:1, 600:1, 500:1, 400:1, 350:1, 330:1, 300:1, 250:1, 225:1, 200:1, 175:1, 150:1, 125:1, 100:1, 75:1, 50:1, 40:1, 30:1, 20:1, 15:1, 10:1 or 1:1. Ratios sometimes are determined on a weight per weight basis (e.g., mg to mg), mole to mole basis, concentration to concentration basis (e.g., mg/ml to mg/ml, molarity to molarity) or sometimes on a weight per volume basis (e.g., mg to ml). For embodiments in which multiple types of matrix or multiple types of nanoparticles are included in a composition, the ratios are applicable to total matrix and total nanoparticles.

A nanoparticle/matrix composition sometimes comprises an additive in addition to a matrix. An additive sometimes improves MALDI MS spectrum quality by enhancing ionization and/or sample preparation. An additive sometimes reduces adduct formation and/or improves sample crystallization.

An additive sometimes is a free radical scavenger. A free radical scavenger suitable for use in MALDI MS analysis can be used, non-limiting examples of which include ascorbic acid, retinol, tocotrienol, tocopherol, coenzyme Q10, melatonin, lycopene, lutein, alpha-carotene, beta-carotene, zeaxanthin, astaxanthin, canthaxanthin, flavones (e.g., luteolin, apigenin, tangeritin), favonols (e.g., quercetin, kaempferol, myricetin, isorhamnetin, proanthocyanidins), favanones (e.g., hasperetin, naringenin, eriodictyol), isoflavone phytoestrogens (e.g., genistein, daidzein, glycitein), stilbenoids (e.g., resveratrol, pterostilbene), anthocyanins (e.g., cyaniding, delphinidin, malvidin, pelargonidin, peonidin, petunidin), phenolic acids and esters (e.g., ellagic acid, gallic acid, salicylic acid, rosmarinic acid, cinnamic acid, chlorogenic acid, chicoric acid, gallotannins, ellagitannins), nonfalvonoid phenolics (e.g., curcumin, xanthones, silymarin, eugenol) and organic antioxidants (e.g., citric acid, oxalic acid, phytic acid, lignan, uric acid, N-acetylcysteine), the like and combinations thereof. An additive sometimes is ammonium citrate (AC), di-ammonium citrate (DAC), ammonium oxalate (AO), the like or combination thereof. Non-limiting examples of additives are described in U.S. Pat. No. 7,888,127, naming Thomas Becker as inventor and entitled METHODS FOR REDUCING ADDUCT FORMATION FOR MASS SPECTROMETRY ANALYSIS.

An additive can be dissolved or suspended in a suitable solvent (e.g., water) and sometimes is in liquid form when combined with a matrix in a composition. An additive sometimes is substantially free of impurities and is purified, and sometimes an additive is not substantially pure and is purified by a suitable method to remove impurities (e.g., ion-exchange resin purification). An additive (e.g., in solid or liquid from) sometimes is combined with a liquid composition comprising a matrix. An additive can be (i) combined with a matrix before the matrix is combined with nanoparticles, (ii) combined with a matrix after the matrix is combined with nanoparticles, (iii) combined with a matrix before an analyte is combined with the matrix, or (iv) combined with a matrix before a sample is deposited on a substrate. An additive often is combined with a matrix in solution before depositing a sample onto a substrate, where the solution may consist essentially of matrix (i.e., the matrix may contain one or more non-essential impurities at relatively low amounts (e.g., about 10%, 5%, 1%, 0.1% 0.01%, 0.001%, 0.0001%, 0.00001% or less of the amount of matrix, e.g., about 1 ppm, 0.1 ppm, 0.01 ppm, 0.001 ppm, 0.0001 ppm, 0.00001 ppm or less of matrix)).

An additive sometimes is present in a nanoparticle/matrix composition in an amount of about 1% to 90% (wt/wt) or about 10% to about 40% (wt/wt) (e.g., about 10%, 15%, 20%, 25% 30%, 35%, or 40%). Such amounts of an analyte sometimes are present in a sample before the sample is deposited onto a substrate. An additive sometimes is added to a composition comprising about 10 micrograms per milliliter (ug/ml) to about 400 ug/ml of a matrix, about 75 ug/ml to about 300 ug/ml of a matrix, or about 100 ug/ml to about 250 ug/ml of a matrix (e.g., about 100, 120, 130, 140, 150, 160, 170, 180, 190, 200, 210, 220, 230, 240, or about 250 ug/ml of a matrix). The amounts of matrix noted in the previous sentence are applicable to a composition comprising one type of matrix and to a composition comprising a total amount of multiple types of matrix. An additive sometimes is in a molar ratio relative to matrix (i.e., moles additive to moles mass spectrometric matrix) of about 1:1 to about 1:25 (e.g., about 1:20, 1:19, 1:18, 1:17, 1:16, 1:15, 1:14, 1:13, 1:12, 1:11, 1:10, 1:9, 1:8, 1:7, 1:6, 1:5, 1:4, 1:3 or 1:2).

A nanoparticle/matrix composition sometimes comprises 3-HPA and optionally ascorbic acid and/or ammonium oxalate. In some embodiments, 3-HPA is present at a concentration of about 100 mM to about 500 mM, about 150 mM to about 300 mM, or about 225 mM in a nanoparticle/matrix composition (e.g., 150 mM, 160 mM, 170 mM, 180 mM, 190 mM, 200 mM, 210 mM, 220 mM, 230 mM, 240 mM, 250 mM, 260 mM, 270 mM, 280 mM, 290 mM or about 300 mM). A nanoparticle/matrix composition sometimes comprises ascorbic acid and/or ammonium oxalate each at a concentration of about 0.5 mM to about 500 mM or 5 mM to about 100 mM (e.g., about 5 mM, 10 mM, 15 mM, 20 mM, 25 mM, 30 mM, 35 mM, 40 mM, 45 mM or about 50 mM). In certain nanoparticle/matrix compositions, 3-HPA is present at about 200 to about 250 mM, ascorbic acid is present at about 15 to about 25 mM and ammonium oxalate is present at about 15 to about 25 mM. A nanoparticle/matrix composition sometimes comprises, consists essentially of, or consists of 3-HPA, ascorbic acid, ammonium oxalate and nanoparticles comprising $SiO_2$, and optionally includes an analyte. A composition that "consists essentially of" 3-HPA, ascorbic acid, ammonium oxalate and nanoparticles, and optionally analyte, can contain one or more contaminants present at relatively low levels (e.g., less than about 10%, 1%, 0.1% 0.01%, 0.001%, 0.0001%, 0.00001% of the amount of the combined amount of 3-HPA, ascorbic acid, ammonium oxalate and nanoparticles, and optionally analyte).

Substrates

A substrate generally is an insoluble support onto which a sample can be deposited and analyzed by MALDI MS or other suitable MS format. A substrate sometimes comprises a flat surface or substantially flat surface configured to receive one or more samples at discrete domains. Domains sometimes are referred to as locations, loci or regions herein.

In some embodiments, a domain includes a topology or feature configured to retain a sample at the domain after the sample is deposited. A topology or feature therefore often is referred to herein as a containment structure. A substrate, and a domain of a substrate, can include any containment structure or combination of containment structures configured to isolate a sample. A containment structure often is configured to isolate a sample after the sample has been deposited onto the substrate and as the sample dries (e.g., and crystallizes) at a domain. A containment structure often is configured to contain a sample after the sample has dried (e.g., and crystallized). For a sample comprising matrix and nanoparticles in crystalline form on a substrate, in certain embodiments substantially all of the crystalline form is within each containment structure and substantially no crystalline form is outside each containment structure.

A containment structure sometimes is a structural obstacle that interferes with movement of a sample on the substrate (e.g., a depression or projection on a flat or substantially flat substrate). A containment structure sometimes functions as an obstacle that that interferes with movement of a sample via chemical interaction, surface energy interaction (e.g., hydrophilic interaction, hydrophobic interaction, or combination thereof), surface texture interaction, the like or combination thereof. Accordingly, a containment structure sometimes comprises a depression (e.g., a well) disposed in or on a substrate, a projection (e.g., a post) disposed on or in a substrate, a surface having a surface energy different than the surface energy of an adjacent surface on the substrate (referred to herein as a "differential surface energy region"), a surface having a texture (e.g., roughness) different than the texture of an adjacent surface (referred to herein as a "differential texture region"), the like and combinations thereof. For example, a depression or projection may include a relatively hydrophilic surface adjacent to a relatively hydrophobic surface (e.g., a depression or well may include a surface (e.g., bottom surface) that is relatively hydrophilic, and another surface that is relatively hydrophobic (e.g., a wall surface)).

A surface of a substrate region that does not include a containment structure sometimes (i) is flat or substantially flat and sometimes comprises substantially no elevations, substantially no elevation differences and/or substantially no depressions, (ii) is substantially smooth, (iii) includes one or more features independently chosen from etching, photoresist, offset surface, ridge, projection, post, pin, stage, depression, dent, well, raised well, hydrophilic surface (e.g., relatively hydrophilic surface), hydrophobic surface (e.g., relatively hydrophobic surface), rough surface (e.g., relatively rough surface), smooth surface (e.g., relatively smooth surface) and the like, (iv) does not include one or more features independently chosen from etching, photoresist, offset surface, ridge, projection, post, pin, stage, depression, dent, well, raised well, hydrophilic surface (e.g., relatively hydrophilic surface), hydrophobic surface (e.g., relatively hydrophobic surface), rough surface (e.g., relatively rough surface), smooth surface (e.g., relatively smooth surface) and the like. A domain that includes a containment structure sometimes (i) is flat or substantially flat and sometimes comprises substantially no elevations, substantially no elevation differences and/or substantially no depressions, (ii) is substantially smooth, (iii) includes one or more features independently chosen from etching, photoresist, offset surface, projection (e.g., ridge, post, pin, stage), depression (e.g., dent, pit, well), raised well, hydrophilic surface (e.g., relatively hydrophilic surface), hydrophobic surface (e.g., relatively hydrophobic surface), rough surface (e.g., relatively rough surface), smooth surface (e.g., relatively smooth surface) and the like, (iv) does not include one or more features independently chosen from etching, photoresist, offset surface, ridge, projection, post, pin, stage, depression, dent, well, raised well, hydrophilic surface (e.g., relatively hydrophilic surface), hydrophobic surface (e.g., relatively hydrophobic surface), rough surface (e.g., relatively rough surface), smooth surface (e.g., relatively smooth surface) and the like.

Any depression that localizes, or in part localizes, a sample at a domain may serve as a containment structure. Similarly, any projection that localizes, or in part localizes, a sample at a domain may serve as a containment structure. A depression or projection often includes a point and/or a surface offset from an adjacent surface. A point or a surface sometimes is offset from an adjacent surface by at least about 1 micrometer, and sometimes is offset by about 1 micrometers to about 500 micrometers (e.g., about 1, 2, 3, 4, 5, 6, 7, 8, 9, 10, 15, 20, 25, 30, 40, 50, 60, 70, 75, 80, 90, 100, 150, 200, 250, 300, 350, 400, 450 micrometers). An offset surface or point can be above or below a surface of a substrate (e.g., a flat or substantially flat surface of a substrate). A projection sometimes is of a height, measured from the substrate surface, of about 1 micrometer to about 500 micrometers (e.g., about 1, 2, 3, 4, 5, 6, 7, 8, 9, 10, 15, 20, 25, 30, 40, 50, 60, 70, 75, 80, 90, 100, 150, 200, 250, 300, 350, 400, 450 micrometers). A depression sometimes is of a depth, measured from the substrate surface, of about 1 micrometer to about 500 micrometers (e.g., about 1, 2, 3, 4, 5, 6, 7, 8, 9, 10, 15, 20, 25, 30, 40, 50, 60, 70, 75, 80, 90, 100, 150, 200, 250, 300, 350, 400, 450 micrometers). An offset, height or depth sometimes is an average, mean, median, nominal, minimum or maximum offset, height or depth, respectively, for a containment structure.

A containment structure can be of any suitable width for retaining a sample at a domain. A maximum effective width of a containment structure, as measured at the substrate surface, sometimes is about 4 millimeters (mm) or less. The substrate surface typically is at a transition to a depression and above an offset surface or point in a depression, or at a transition of a projection and below an offset surface or point of the projection. An effective width sometimes generally is the width in which the perimeter of a containment structure fits, and sometimes is the span of a rectangular structure or a diameter of a circular structure, for example. A maximum effective width of a containment structure, as measured at the substrate surface, sometimes is about 0.1 millimeters to about 5 millimeters (e.g., about 5, 4, 3, 2, 1.5, 1, 0.9, 0.8, 0.7, 0.6, 0.5, 0.4, 0.3, 0.2 or about 0.1 millimeters or less). An internal effective width of a depression (e.g., a well) sometimes is about 5 millimeters or less (e.g., about 5, 4, 3, 2, 1.9, 1.8, 1.7, 1.6, 1.5, 1.4, 1.3, 1.2, 1.1 millimeters or less, and sometimes is about 1 millimeter or less (e.g., about 0.9, 0.8, 0.7, 0.6, 0.5, 0.4, 0.3, 0.2, 0.1 millimeters or less). In some embodiments a depression (e.g., a well) is about 0.1 mm×0.1 mm, 0.2 mm×0.2 mm, 0.3×0.3 mm or about 0.4×0.4 mm square. A projection (e.g., pin, post, ridge) sometimes comprises a width of about 4 mm to about 0.1 mm or about 2 mm to about 0.1 mm (e.g., about 4, 3, 2, 1.5, 1, 0.9, 0.8, 0.7, 0.6, 0.5, 0.4, 0.3, 0.2 or about 0.1 mm).

A projection or depression sometimes includes one or more walls. A wall surface sometimes is about perpendicular to an adjacent surface, and sometimes is at an angle of greater than or less than 90 degrees with respect to the adjacent surface. A transition from one surface to another sometimes is curved (e.g., a surface defined by a radius) or not curved (e.g., angled, beveled, stepped surfaces). Thus, a transition from one surface to another for a projection or depression sometimes comprises an edge, bump, point, recess, the like or combination thereof. Without being limited by theory, one or more edges or points present in a containment structure can function as a seed site for sample crystallization (e.g., matrix crystallization). A projection or depression can comprise a structure having any suitable vertical profile or cross section, and any suitable horizontal profile or cross-section, non-limiting examples of which include oval, circle, ellipse, polygon (e.g., square, rectangle, triangle, tetragon, pentagon, hexagon, heptagon, octagon, nonagon, decagon), pyramidal, reverse pyramidal, frustrum, conical, reverse conical, arced, bowl-shaped, U-shaped, V-shaped, stepped, the liked and combinations thereof. A bottom of a depression (e.g., a well) can be any suitable configuration (e.g., flat, pointed, round).

Any differential surface energy region that localizes, or in part localizes, a sample to a domain may serve as a containment structure present at a domain. A containment structure comprising a differential surface energy region sometimes comprises (i) a hydrophilic surface adjoining, or surrounded by, a relatively hydrophobic surface, or (ii) is a relatively hydrophilic surface adjoining, or surrounded by, a hydrophobic surface. A combination of a relatively hydrophilic surface and relatively hydrophobic surface can contain a sample. Without being limited by theory, a relatively hydrophobic surface often repels a dispensed liquid sample and a relatively hydrophilic surface often does not repel, and retains, the dispensed sample. Hydrophilic regions (e.g., hydrophilic domains) often occupy less surface area than hydrophobic regions, and hydrophilic regions often are uniformly spaced on the substrate (e.g., in an array). In some embodiments, hydrophobic regions occupy less surface area than hydrophilic regions on a substrate. In some embodiments, substantially all of the surface area of each domain on a substrate is hydrophobic. In certain embodiments, substantially all of the surface area of a substrate, including domains, is hydrophobic. In some embodiments, substantially all of the surface area of all or a subset of projections present on a substrate, and/or the surface area of all or a subset of depressions present in a substrate, are hydrophilic and the remaining surface area of the substrate is hydrophobic. In certain embodiments, the surface area of all projections and depressions present on or in a substrate, and the remaining surface area of the substrate, are hydrophobic.

A hydrophilic region sometimes is characterized by a contact angle of less than 90 degrees against water, and sometimes is characterized by a contact angle of about 20 degrees to about 85 degrees against water (e.g., about 25, 30, 35, 40, 45, 60, 65, 60, 75, 80 degrees). A hydrophilic region sometimes is characterized by a contact angle of less than about 20 degrees or less, or 13 degrees or less, against water (e.g., less than or equal to 19, 28, 17, 16, 25, 14, 13, 12, 11, 10, 9, 8, 7, 6, 5, 4, 3, 2 or 1 degrees against water). A hydrophobic region sometimes is characterized by a contact angle of greater than 90 degrees against water, and sometimes is characterized by a contact angle against water of about 95 degrees to about 180 degrees, or about 95 degrees to about 150 degrees, or about 95 degrees to about 120 degrees (e.g., about 100, 105, 110, 115, 120, 125, 130, 140, 150, 160, 170 degrees). A substrate and/or a hydrophobic surface of a substrate often is substantially non-retroreflective. A contact angle differential between a hydrophobic region and hydrophilic region sometimes is greater than or equal to a differential of about 20 degrees to about 120 degrees (e.g., about 25, 30, 35, 40, 45, 50 55, 60, 65, 70, 75, 80, 85, 90, 95, 100, 110 degrees against water).

A region can be made hydrophobic, substantially hydrophobic or more hydrophobic by treating a surface under certain conditions, such as with a hydrophobic substance (e.g., resulting in a hydrophobic coating) or conditions that yield a hydrophobic surface. Non-limiting examples of hydrophobic treatments are treating a surface with gold, an alkane-thiol or an alkane silane (e.g., dimethyldichlorosilane (DMDCS)). A region can be made hydrophilic, substantially hydrophilic or more hydrophilic by treating a surface under specific conditions, such as with a hydrophilic substance (e.g., resulting in a hydrophilic coating). Non-limiting examples of hydrophilic treatments include applying a photoresist layer or photoresist coating to a surface, or exposing a surface to an oxidizing force (e.g., corona discharge, plasma treatment, laser treatment).

Any differential texture region that localizes a sample to a domain may serve as a containment structure present at a domain. A differential texture region sometimes comprises (i) a smooth or substantially smooth region or region having a first texture adjoining or surrounded by a region having a second texture, or (ii) a region having a second texture surrounded by a smooth or substantially smooth region or region having a first texture, where the second texture is rougher than the first texture. A textured region sometimes comprises ridges, barbs, grooves, grains, embossed features, etches, pores, pits, lines, scratches, scores, scrapes, cuts, carvings, incisions, the like and combinations thereof. Roughness can be quantified by an area roughness parameter, areal roughness parameter, profile roughness parameter, amplitude parameter, slope spacing and counting parameter, bearing ratio parameter, the like and combinations thereof.

Domains sometimes are configured in an array on a substrate. Any suitable array may be present on a substrate, non-limiting examples of which include a 1×8, 1×12, 2×3, 3×3, 4×4, 4×6, 5×5, 6×6, 7×7, 8×8, 8×12, 9×9, 10×10, 12×12, 16×24, 32×48, or 64×96 array, and the like. An array sometimes comprises rows having an alternating number of domains. In some embodiments an array includes a suitable number of regularly spaced domains, non-limiting examples of which include 2, 4, 6, 8, 9, 12, 16, 24, 25, 36, 48, 49, 64, 81, 96, 100, 144, 384, and 1536 domains. An array sometimes comprises domains that are equidistant or substantially equidistant from each other, and the top view center of each domain often is the same distance from the top view center of adjacent domains. The distance between domain centers can be referred to as a pitch. A 1×12 array sometimes has a pitch of about 9 mm; a 4×6 or a 1×8 array sometimes has a pitch of about 4.5 mm; an 8×12 array sometimes has a pitch of about 2.25 mm; a 16×24 array sometimes has a pitch of about 1.125 mm; and a 32×48 array sometimes has a pitch of about 0.5625 mm. Sometimes an array is substantially uniform.

A substrate may include, or be manufactured from, any material suitable for conducting MALDI MS, non-limiting examples of which include silicon, silica, glass (e.g. glass, controlled-pore glass (CPG)), nylon, Wang resin, Merrifield resin, Sephadex, Sepharose, cellulose, magnetic beads, Dynabeads, a metal or metal surface (e.g. steel, metal alloys, gold, silver, stainless steel, aluminum, silicon and copper), a plastic or polymer (e.g., polyethylene, polypropylene, polystyrene, polyvinyl chloride (PVC), polymethyl metaacrylate (PMMA, Plexiglas), polyamide, polyester, polytetrafluoroethylene, Teflon, polyvinylidenedifluoride (PVDF)), a cyclo olefin polymer, a gold coated cyclo olefin polymer, various coatings (e.g., fluorocarbon polymers (e.g., fluorinated ethylene-propylene, polytetrafluoroethylene), photoresist, dimethyldichlorosilane (DMDCS coating)), the like or combinations thereof. In some embodiments a substrate is coated with a suitable material. Substrate materials generally are inert or substantially inert with respect to an analyte, matrix, nanoparticles, additives and MS conditions. A substrate can be provided as any structure suitable for conducting MALDI MS, non-limiting examples of which include a bead, capillary, disk, filter, dipstick, membrane, wafer, comb, pins (e.g., arrays of pins suitable for combinatorial synthesis or analysis), the like or combinations thereof. In some embodiments a substrate is a plate and sometimes is a chip (e.g., a silicon chip).

Mass Spectrometry Analysis

An analyte sometimes is analyzed by MALDI MS using one or more compositions and methods described herein. A sample often is deposited onto a substrate as part of preparing a sample for MALDI MS analysis. A sample often is a portion (e.g., volume, aliquot) of a matrix/nanoparticle composition, optionally including an analyte, additive, the like or combination thereof. A sample often is deposited in liquid form onto one or more domains of a substrate and the deposited sample often is exposed to drying conditions. Any suitable process for depositing a sample onto a domain of a substrate can be utilized. A sample can be deposited manually onto one or more domains by an operator using a suitable device (e.g., manual pipettor). Depositing a sample onto one or more domains of a substrate sometimes is automated, and a suitable automated liquid dispensing instrument may be utilized. A sample deposited onto a substrate at a domain sometimes is referred to herein as a spot, and a spot may be in a substantially liquid form, a substantially solid form (e.g., crystalline form), the like or combination thereof. A deposited sample sometimes transitions from liquid phase to solid phase (e.g., crystalline form) on the substrate as part as part of a sample drying process. Drying conditions (e.g., crystallization conditions) sometimes are not controlled (e.g., drying under ambient conditions) and sometimes are controlled. Under controlled drying conditions, temperature, pressure, humidity, air, gases, the like and combinations thereof sometimes are controlled. Drying (e.g., crystallization) sometimes takes place in a chamber (e.g., a vacuum chamber, humidity chamber, incubator, oven).

In certain embodiments, a sample on a substrate is dried (e.g., crystallized) at (i) ambient pressure (e.g., about 14 psi, about 101.35 kilopascals), (ii) in a vacuum, (iii) at ambient or room temperature, (iv) at ambient relative humidity, (v) at a temperature greater than or less than 25 degrees Celsius or room temperature (e.g., at a temperature of about 15 to about 40 degrees Celsius, about 15 to about 35 degrees Celsius or about 20 to about 30 degrees Celsius (e.g., about 20, about 21, about 22, about 23, about 24, about 25, about 26, about 27, about 28, about 29 or about 30 degrees Celsius)), (vi) at a humidity greater than or less than ambient humidity (e.g., at a relative humidity of about 30% to about 70% or about 45% to about 55% (e.g., about 45, 46, 47, 48, 49, 50, 51, 52, 53, 54, or about 55% relative humidity), (vii) the like or (viii) combination thereof.

A sample deposited onto a substrate often has a greater spot width (e.g., diameter) before drying than after drying. A deposited sample often shrinks in width as it dries, and the sample often is substantially contained and localized to a domain by a containment structure in certain substrates described herein. A dried (e.g., crystallized) sample often is substantially contained within the perimeter of a containment structure on certain substrates described herein.

An average, mean, median, nominal, maximum or minimum width (e.g., diameter) of a sample at a substrate domain sometimes is about 0.1 mm to about 5 mm, or greater, and sometimes is about 0.1 mm to about 4 mm, about 0.1 mm to about 2 mm, or about 0.2 mm to about 1 mm (e.g., about 0.2, 0.3, 0.4, 0.5, 0.6, 0.7, 0.8, 0.9, 1.0, 1.1, 1.2, 1.3, 1.4, 1.5, 1.8, 1.9, 2.0 mm). An average, mean, median, nominal, maximum or minimum depth (i.e., thickness, z-dimension) of a sample at a substrate domain sometimes is about 4 mm to about 0.001 mm, about 2 mm to about 0.01 mm, about 1 mm to about 0.01 mm, about 0.5 mm to about 0.005 mm, about 0.2 mm to about 0.005 mm, about 0.2 mm to about 0.05 mm, about 0.5 mm to about 0.2 mm, or about 0.02 mm to about 0.01 mm (e.g., about 1000, 900, 800, 700, 600, 500, 400, 300, 200, 175, 150, 125, 100, 95, 90, 85, 80, 75, 70, 65, 60, 55, 50, 45, 40, 35, 30, 25, 20, 15, 10, 5 or about 1 micrometer (um) or less). The depth and/or width of each sample on a substrate sometimes varies independently by less than about 15%, 10%, 5%, 2%, 1%, 0.1% or 0.01%. The depth and/or width of multiple samples deposited on a substrate sometimes vary independently by about 15% or less, 10% or less, 5% or less, 2% or less, 1% or less, 0.1% or less or 0.01% or less.

For embodiments in which a sample crystallizes, crystal topography often is not rough or jagged and there often are substantially no relatively large or needle-like crystals. Crystalline samples often are characterized as having relatively small, homogeneous and significantly uniform crystals that often resemble snowball-like crystal structures and have relatively high uniformity. The challenge of reducing crystal heterogeneity often becomes greater as the size of a domain increases (e.g., 1 mm or wider). In some embodiments, all or substantially all crystals in a sample at a domain have a length of less than 200 um, and sometimes have a length of about 1 um to about 200 um or about 10 um to about 100 um (e.g., about 5, 10, 15, 20, 25, 30, 35, 40, 45, 50, 60, 70, 80 or 90 um). In certain embodiments, a sample at a domain includes no crystals, or substantially no crystals, having a length of 200 um or greater (e.g., 300 um, 400 um, 500 um, 600 um, 700 um, 800 um, 900 um, 1000 um or greater). The foregoing crystal parameters often are applicable to all or substantially all samples on a substrate.

Analyzing an analyte sometimes includes determining a mass of one or more ions arising from the analyte after the analyte has been deposited onto the substrate. Prior to conducting MS analysis, sample comprising an analyte and a matrix sometimes is deposited on a substrate. A sample comprising a matrix and no analyte sometimes is deposited on a substrate, and an analyte then is deposited on the matrix that was deposited on the substrate. In the latter embodiments, a crystalline matrix already deposited on a substrate sometimes dissolves when a solution comprising an analyte is deposited on the matrix, and the matrix then re-crystallizes after analyte deposition.

For MALDI MS analysis, a substrate comprising deposited samples can be placed in a mass spectrometer, and a sample on the substrate can be ionized and volatilized. A sample often is contacted with ionization energy, and a sample sometimes is ionized by a laser pulse, as part of MALDI MS. Components of a sample often are transported into a gas phase after the sample is contacted with ionization energy. A voltage can be applied to ionized sample components, which can accelerate ions into a field-free flight tube. Ions in the ion source often are accelerated to different speeds due to differences in mass. Smaller ions often reach a detector earlier than the larger ions and the mass of the different ion species can be determined. Accordingly, mass, relative mass, difference in mass, mass to charge ratio, relative mass to charge ratio, difference in mass to charge ratio, the like and combinations thereof, of ionized sample components can be determined as part of MS analysis. One or more components of known composition and mass can be used as a reference (e.g., standards) to determine the mass and/or composition of one or more analytes. A reference or standard can be analyzed separate from a sample (e.g., external standard, external reference) and/or can be placed in a sample and analyzed in the sample (e.g., internal standard, internal reference).

Mass spectra quality can increase when using a composition and/or substrate described herein for MADLI MS analysis of an analyte, and time-of-flight deviation for ions often decreases as a result of using a composition and/or substrate described herein. Use of a composition and/or substrate described herein can result in a reduction of double peaks for an ion species in MALDI mass spectra, and may result in removal of double peaks for one or more or all ion species in MALDI mass spectra. Use of a composition and/or substrate described herein can result in about a 2-fold to about a 10-fold increase in accuracy (i.e., accuracy improvement), or about a 2-fold to about a 5-fold increase in accuracy (e.g., about a 3-fold or 4-fold increase in accuracy). Use of a composition and/or substrate described herein can result in an increase in accuracy of up to about 20% (e.g., up to about a 1, 2, 4, 5, 6, 7, 8, 9, 10, 11, 12, 13, 14, 15, 16, 17, 18 or 19% increase in accuracy). Accuracy can be expressed for a single mass reading or measurement, and sometimes is expressed according to the following equation in terms of parts per million (ppm) for a single reading or measurement.

$$\text{mass measurement error(accuracy)} = ((M_{obtained} - M_{theoretical})/M_{theoretical}) \times 10^6$$

Mass accuracy for a substrate sample having a relatively smooth crystal topology sometimes is about 200 ppm to about 500 ppm and mass accuracy for a substrate sample having a relatively rough crystal topology sometimes is about 200 ppm to about 2,000 ppm.

In addition to MALDI MS, a non-limiting example of another mass spectrometry format that can be improved by a composition or substrate described herein is Laser Desorption Mass Spectrometry (LDMS).

BRIEF DESCRIPTION OF THE DRAWINGS

The drawings illustrate embodiments of the technology and are not limiting. For clarity and ease of illustration, the drawings are not made to scale and, in some instances, various aspects may be shown exaggerated or enlarged to facilitate an understanding of particular embodiments.

EXAMPLES

Figure 1:
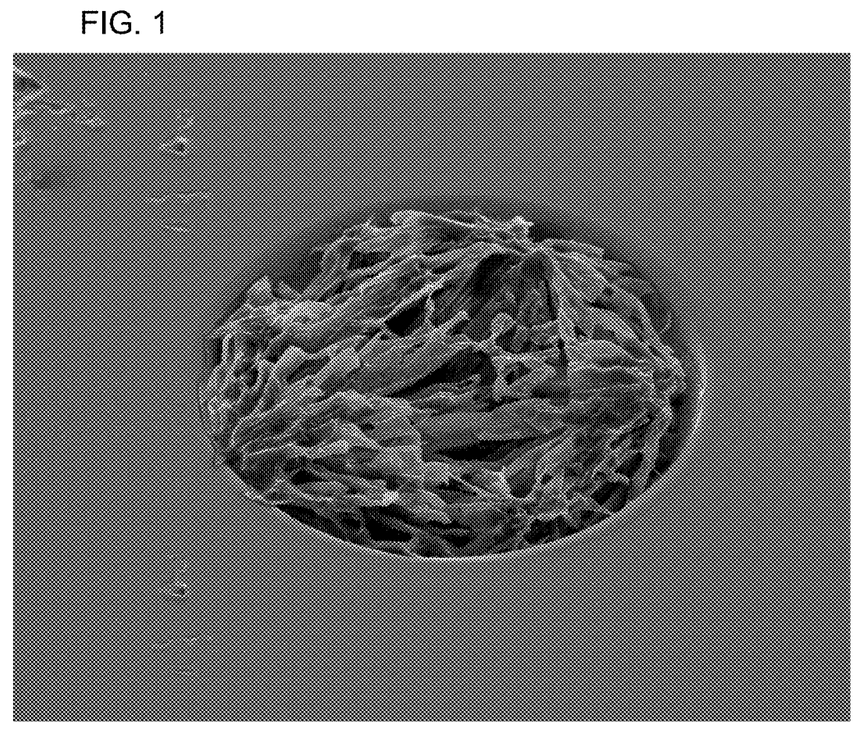
FIG. 1 shows a scanning electron microscopy (SEM) image of substrate comprising an embodiment of a containment structure (e.g., a well) and a crystallized matrix. The containment structure shown is about 200 µm wide and about 20 µm deep.
Figure 2A:
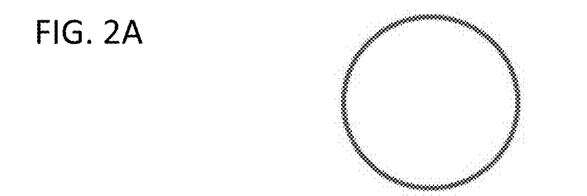
FIG. 2A shows a top view schematic of an embodiment of a containment structure (e.g., a round well)
Figure 2B:
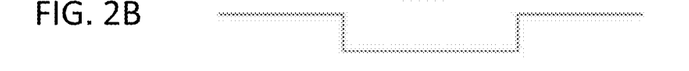
FIG. 2B shows a cross-sectional side view thereof.
Figure 3A:
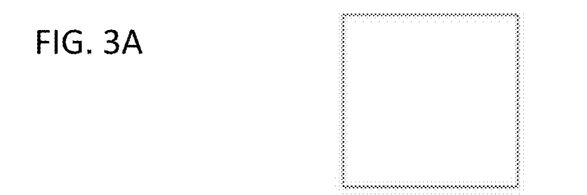
FIG. 3A shows a top view schematic of an embodiment of a containment structure (e.g., a square well)
Figure 3B:
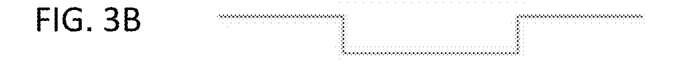
FIG. 3B shows a cross-sectional side view thereof.
Figure 4A:
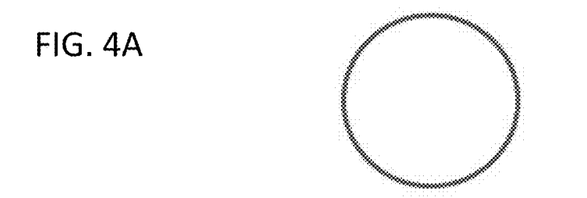
FIG. 4A shows a top view schematic of an embodiment of a containment structure (e.g., a round post)
Figure 4B:
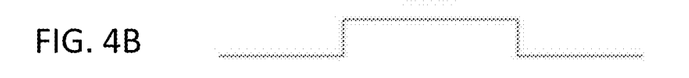
FIG. 4B shows a cross-sectional side view thereof.
Figure 5A:
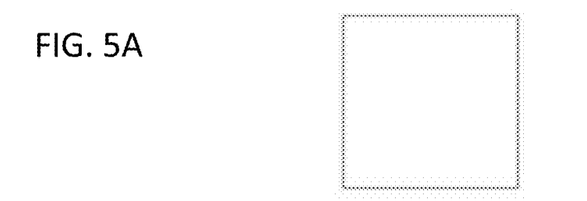
FIG. 5A shows a top view schematic of an embodiment of a containment structure (e.g., a square post)
Figure 5B:
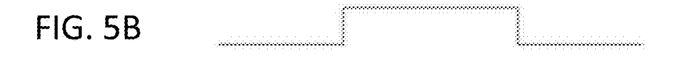
FIG. 5B shows a cross-sectional side view thereof.

The examples set forth below illustrate certain embodiments and do not limit the technology.

Example 1

Preparation of Crystals

Fumed silica particles (SiO2, 14 nm) were purchased from Sigma/Aldrich (S5505-100G). Since these particles are easily air-borne and thus, not easy to transfer to a scale, the content of the whole container (100 g) was thoroughly mixed with 2 liter of nanopure water to yield a concentration of 50 mg/ml. Aliquots were further diluted with nanopure water to yield working solutions of 2.5, 3, 3.5 and 5 mg/ml, respectively. Twenty ml of each working solution was transferred to a 50 ml falcon tubes and 25 mg/ml of protonated (H+-form) ion exchange resin was added for clean-up. For proper mixing, the falcon tubes were then rotated for 10 min. The resin was then allowed to separate (settle) from the dispersed silica. Silica particles in solution were aspirated and removed from the resin. Since silica particles stay in suspension for days, no change in concentration was expected during matrix formulation and dispensation. Matrix solution was made fresh every day from stock solutions.

New Matrix was prepared by adding 1000 µl of 300 mM 3-Hydroxypicolinic Acid (3-HPA), 133 µl of 200 mM ascorbic acid and 133 µl of 200 mM ammonium oxalate except for the addition of 67 ul of water which was replaced by the addition of 67 ul dispersed silica from the working solutions. The resulting matrix solution contained final silica concentrations of 125, 150, 175 and 250 µg/ml, respectively. For convenience, the following naming convention for the silica spiked new matrix will be used onward as: Gen2-125 (125 ug/ml Silica), Gen2-150 (150 ug/ml Silica), Gen2-175 (175 ug/ml Silica), Gen2-250 (250 ug/ml Silica).

Silanated 24-type SpectroChips with 1 mm domains (diameter) were loaded on a 10× scoutplate and wiped 2× with acetone to completely remove the photoresist domains, followed by a wipe with isopropanol and a final dry wipe. The complete removal of the photoresist domain eliminates the variability in cleanliness and topology, which can influence matrix crystallization. The exposed hydrophilic $SiO_2$ anchors are flush with the hydrophobic surrounding and free from possible manufacturing contamination (e.g., wafer cut, barcode scribing, etc.). Great care was taken once the photoresist was removed because the exposed $SiO_2$ anchors (e.g., containment structures) are prone to contamination from the ambient. Absorption of impurities can result in an unwanted increase in the contact angle. Therefore, matrix was applied shortly (within 2 h) after $SiO_2$ exposure.

A matrix dispenser was built using an pressure driven positive displacement unit. A commercially available controller (1500XL, EFD) was used for positive/negative pressure supply, and pulse duration control. The controller was connected to a nitrogen container (200 L) equipped with a pressure regulator to adjust the controller's input pressure. Matrix solution was loaded into a 5 ml cartridge (EFD), which connects to the pressure controller. The cartridge was equipped with a crimped teflon tip (EFD, i.d. crimp 0.15 mm). In addition, the cartridge was been modified to allow the connection to a matrix reservoir for easy refill. The connection between reservoir and cartridge consists of a high grade silicone tubing (Cole Parmer), which can be closed with a tube clamp. The cartridge was mounted to an adjustable mounting bracket on a programmable xyz dispensing robot (Janome). The xyz robot drives the pressure controller via TTL signal. For dispensing, the cartridge was pressurized for a short pulse duration time, forcing a matrix droplet to be dispensed. Between dispensations, a slight negative pressure was applied to the cartridge to prevent the dispensing tip from leaking matrix. Within the current setup the following parameter were used to dispense 1 µl/pad:

Pulse duration time, 0.005 sec.
Positive pressure, 19-32 psi
Negative pressure, 1.2-1.5 psi Each day a new teflon tip was installed and the dispense parameters were adjusted. The dispense volume of 1 µl was verified from 3 different positions, using 1 µl glass capillaries (Drummond Scientific).

For matrix dispensation, a 10× scoutplate carrying 9 wiped SpectroChips and one non-wiped positioning chip was placed onto the xyz robot. Prior to the automated dispensing procedure, the dispensing tip was adjusted to a pre-defined position. After dispensation, the matrix solution was refilled to obtain optimal hydrostatic pressure throughout the following dispense period. Dispensing of all 10 chips takes <6 min. including, positioning and matrix refill.

Subsequently after matrix deposition (0.8-1.2 µl/domain) the chip carrying scoutplates were placed onto heated plates of a storage tower inside a humidity chamber. Drying conditions in the humidity chamber were found to be optimal at 21° C. and 50% relative humidity with the tower temperature at 30° C. For chip drying, the scoutplates were placed onto temperature controlled trays (by water circulation) of a plate stacker with 11 scoutplate positions. The plate stacker was located inside a temperature and humidity controllable chamber (Parameter Generation Control, Inc.).

Results

Smooth and snowball like matrix crystals were observed from new matrix containing 125 μg/ml silica. At 250 μg/ml a slight decrease in the signal to noise ratio (SNR) obtained from MassCleave samples was observed. Drying conditions in the humidity chamber were found to be optimal at 21° C. and 50% relative humidity with the tower temperature at 30 C. Under these conditions, the chip yield was 70-80%. Chip yield as determined according to the overall spot structure. For example, a 70-80% yield indicates that 70-80% of the spots were snowball-like in appearance and contained crystals with a length between 10 and 100 um.

Example 2

Use of Nanoparticles and Matrix

Examples 1 to 3 in U.S. patent application Ser. No. 12/014,671 entitled COMPOSITIONS AND PROCESSES FOR IMPROVED MASS SPECTROMETRY ANALYSIS describe mass spectrometry methods for analyzing a nucleic acid analyte using a matrix composition that does not comprise nanoparticles. Such methods can be used to analyze advantageous properties of matrix compositions that comprise nanoparticles, as described in Example 1 herein.

Example 3

Examples of Embodiments

Provided hereafter and non-limiting examples of certain embodiments of the technology.

A1. A matrix assisted laser desorption ionization (MALDI) mass spectrometry (MS) substrate comprising a plurality of samples, which samples comprise nanoparticles and a MALDI MS matrix,
which samples are substantially crystallized,
which matrix is not covalently linked to the nanoparticles, and
which nanoparticles are not in association with a peptide or protein.

A2. The substrate of embodiment A1, wherein the matrix is suitable for mass spectrometry analysis of a nucleic acid.

B1. A matrix assisted laser desorption ionization (MALDI) mass spectrometry (MS) substrate comprising a plurality of samples, which samples comprise nanoparticles and a MALDI MS matrix suitable for mass spectrometry analysis of a nucleic acid,
which samples are substantially crystallized, and
which matrix is not covalently linked to the nanoparticles.

B2. The substrate of embodiment B1, wherein the nanoparticles are not in association with a peptide or protein.

C1. The substrate of any one of embodiments A1, A2, B1 and B2, wherein each of the samples comprises substantially no crystals having a length of 200 um or greater.

C2. The substrate of any one of embodiments A1, A2, B1, B2 and C1, wherein the samples have an average, mean, median, nominal, maximum or minimum width or diameter of 0.2 mm or greater.

C3. The substrate of any one of embodiments A1, A2, B1, B2, C1 and C2, wherein the samples have an average, mean, median, nominal or maximum depth variation of 10% or less.

C4. The substrate of any one of embodiments A1, A2, B1, B2 and C1 to C3, wherein there is substantially no ionic, hydrophobic, hydrogen bond or van der Walls association between the matrix and the nanoparticles.

C5. The substrate of embodiment C4, wherein there is substantially no ionic association between the matrix and the nanoparticles.

C5.1. The substrate of any one of embodiment C4, wherein there is substantially no hydrophobic association between the matrix and the nanoparticles.

C5.2. The substrate of any one of embodiment C4, wherein there is substantially no hydrogen bond association between the matrix and the nanoparticles.

C5.3. The substrate of embodiment C4, wherein there is substantially no van der Walls association between the matrix and the nanoparticles.

C5.4. The substrate of any one of embodiments A1, A2, B1, B2 and C1 to C3, wherein there is substantially no association between the matrix and the nanoparticles.

C6. The substrate of any one of embodiments A1, A2, B1, B2 and C1 to C5.4, wherein the samples comprise a matrix chosen from 2,5-dihydroxybenzoic acid (DHB), ammonium citrate (AC), ascorbic acid and 3-hydroxypicolinic acid (3-HPA).

C7. The substrate of embodiment C6, wherein the samples comprises 3-HPA.

C8. The substrate of any one of embodiments A1, A2, B1, B2 and C1 to C7, wherein the matrix consists essentially of a single matrix.

C8.1. The substrate of embodiment C8, wherein the matrix consists essentially of 3-HPA.

C9. The substrate of any one of embodiments A1, A2, B1, B2 and C1 to C3, wherein the matrix consists essentially of multiple matrix components.

C10. The substrate of any one of embodiments A1, A2, B1, B2 and C1 to C9.1, wherein each of the samples comprises one or more additives.

C11. The substrate of embodiment C10, wherein each of the samples comprises ascorbic acid.

C11.1. The substrate of embodiment C10 or C11, wherein each of the samples comprises ammonium oxalate.

C12. The substrate of any one of embodiments C6 to C11.1, wherein each of the samples consists essentially of 3-HPA, ascorbic acid, ammonium oxalate and the nanoparticles.

C12.1. The substrate of any one of embodiments C10 to C12, wherein the one or more additives are not covalently linked to the nanoparticles.

C12.2. The substrate of any one of embodiments C10 to C12, wherein the one or more additives are not associated with the nanoparticles by an ionic, hydrophobic, hydrogen bond, or van der Walls association.

C12.3. The substrate of any one of embodiments C10 to C12, wherein the one or more additives are not associated with the nanoparticles.

C13. The substrate of any one of embodiments A1, A2, B1, B2 and C1 to C12.3, wherein the nanoparticles have an average, mean, median, nominal, minimum or maximum diameter of about 1 nanometer to about 100 nanometers.

C14. The substrate of embodiment C13, wherein the nanoparticles have an average, mean, median, nominal, minimum or maximum diameter of about 5 nanometers to about 30 nanometers.

C15. The substrate of embodiment C14, wherein the nanoparticles have an average, mean, median, nominal, minimum or maximum diameter of about 10 nanometers to about 20 nanometers.

C16. The substrate of embodiment C15, wherein the nanoparticles have an average, mean, median, nominal, minimum or maximum diameter of about 15 nanometers.

C17. The substrate of any one of embodiments A1, A2, B1, B2 and C1 to C16, wherein the nanoparticles are substantially inert.

C18. The substrate of embodiment C17, wherein the nanoparticles are substantially not derivatized with functional chemical groups.

C19. The substrate of embodiment C17, wherein the nanoparticles substantially do not associate with an analyte.

C20. The substrate of embodiment C17, wherein the nanoparticles form substantially no covalent, ionic, hydrophobic, hydrogen bond or van der Walls association with the an analyte.

C21. The substrate of embodiment C19 or C20, wherein the analyte is a nucleic acid analyte.

C22. The substrate of any one of embodiments A1, A2, B1, B2 and C1 to C21, wherein the nanoparticles substantially do not give rise to MALDI MS signals.

C23. The substrate of any one of embodiments A1, A2, B1, B2 and C1 to C22, wherein the nanoparticles comprise substantially no metal.

C24. The substrate of any one of embodiments A1, A2, B1, B2 and C1 to C22, wherein the nanoparticles comprise, consist essentially of, or consist of one or more metals.

C25. The substrate of embodiment C23 or C24, wherein the one or more metals are chosen from gold, silver, platinum, aluminum, titanium, tantalum and vanadium.

C26. The substrate of embodiment C23 or C24, wherein the one or more metals are one metal and the metal is iron.

C27. The substrate of embodiment C25 or C26, wherein the analyte is a nucleic acid.

C28. The substrate of any one of embodiments A1, A2, B1, B2 and C1 to C27, wherein the nanoparticles substantially do not form multimers.

C29. The substrate of any one of embodiments A1, A2, B1, B2 and C1 to C28, wherein the nanoparticles comprise $SiO_2$.

C30. The substrate of embodiment C29, wherein the nanoparticles substantially are fumed silica particles.

C31. The substrate of any one of embodiments A1, A2, B1, B2 and C1 to C30, wherein the matrix to nanoparticle ratio for each of the samples is about 0.1:1 to about 30,000:1.

C31.1. The substrate of any one of embodiments A1, A2, B1, B2 and C1 to C30, wherein the matrix to nanoparticle ratio for each of the samples is about 1:1 to about 600:1.

C31.2. The substrate of any one of embodiments A1, A2, B1, B2 and C1 to C30, wherein the matrix to nanoparticle ratio for each of the samples is about 13:1 to about 430:1.

C32. The substrate of any one of embodiments A1, A2, B1, B2 and C1 to C31.2, wherein the substrate is chosen from a plate, chip, disk, filter, comb, pin and dipstick.

C33. The substrate of embodiment C32, wherein the substrate is a chip.

C34. The substrate of embodiment C33, wherein the substrate is a silicon chip.

C35. The substrate of any one of embodiments A1, A2, B1, B2 and C1 to C34, wherein the substrate comprises a substantially flat surface.

C36. The substrate of any one of embodiments A1, A2, B1, B2 and C1 to C35, wherein the surface of the substrate comprises hydrophobic regions.

C37. The substrate of any one of embodiments A1, A2, B1, B2 and C1 to C35, wherein the surface of the substrate is substantially hydrophobic.

C38. The substrate of any one of embodiments A1, A2, B1, B2 and C1 to C37, wherein the surface of the substrate comprises hydrophobic regions and relatively hydrophilic regions.

C39. The substrate of embodiment C38, wherein the samples are located on the relatively hydrophilic regions.

C40. The substrate of embodiment C38 or C39, wherein the relatively hydrophilic regions comprise a photoresist layer.

C41. The substrate of any one of embodiments C38 to C39, wherein the relatively hydrophilic regions do not comprise a photoresist layer.

C42. The mass spectrometry of substrate of any one of embodiments C38 to C41, wherein the hydrophobic regions are silanated.

C43. The mass spectrometry of substrate of any one of embodiments C38 to C42, wherein the relatively hydrophilic regions are arranged on the surface of the substrate in an array.

C44. The mass spectrometry of substrate of any one of embodiments C38 to C43, wherein the hydrophobic regions are located on the surface of the substrate around the relatively hydrophilic regions.

C45. The substrate of any one of embodiments C35 to C44, wherein the substantially flat surface of the substrate comprises substantially no elevations and substantially no depressions.

C46. The substrate of embodiment C45, wherein the surface of the substrate comprises substantially no feature chosen from a wafer cut, bar code scribe, photoresist, ridge or combination thereof.

C47. The substrate of any one of embodiments C35 to C44, wherein the surface of the substrate comprises structures of any one of embodiments G1 to G26.

C48. The substrate of any one of embodiments C35 to C47, wherein the substantially flat surface of the substrate is substantially smooth.

C49. The substrate of any one of embodiments A1, A2, B1, B2 and C1 to C48, wherein the samples are disposed on the substrate in an array.

C50. The substrate of any one of embodiments A1, A2, B1, B2 and C1 to C49, comprising about 24 samples.

C51. The substrate of any one of embodiments A1, A2, B1, B2 and C1 to C49, comprising about 96 samples.

C52. The substrate of any one of embodiments A1, A2, B1, B2 and C1 to C49, comprising about 384 samples.

C53. The substrate of any one of embodiments A1, A2, B1, B2 and C1 to C52, wherein one or more of the samples comprise an analyte.

C54. The substrate of embodiment C53, wherein the analyte is chosen from nucleotides, oligonucleotides, polynucleotides, nucleic acid, peptides, proteins, polymers (e.g., synthetic polymer, industrial polymer, plastic polymer), saccharides, polysaccharides, sugars, carbohydrates, lectins, lipids, glycoproteins, lipoproteins, small molecules, small chemical entities, metabolites, natural products, pharmaceuticals, conjugates and combinations thereof.

D1. A method for manufacturing a matrix assisted laser desorption ionization (MALDI) mass spectrometry (MS) substrate of any one of embodiments A1, A2, B1, B2 and C1 to C52, comprising:
  depositing samples comprising the matrix and the nanoparticles at domains on the substrate, and
  exposing the samples to conditions under which the samples crystallize at each of the domains on the substrate.

D2. The method of embodiment D1, wherein the matrix and the nanoparticles are deposited separately at each of the domains.

D3. The method of embodiment D1 or D2, wherein the samples are in a solution, and the solution is deposited at the locations on the substrate.

D4. The method of embodiment D3, wherein the nanoparticles are at a concentration of about 1 micrograms per milliliter to about 500 micrograms per milliliter in the solution.

D5. The method of embodiment D4, wherein the nanoparticles are at a concentration of about 75 micrograms per milliliter to about 300 micrograms per milliliter in the solution.

D6. The method of embodiment D4, wherein the nanoparticles are at a concentration of about 125 micrograms per milliliter or about 250 micrograms per milliliter in the solution.

D6.1. The method of embodiment D6, wherein the matrix is at a concentration of about 1 millimolar (mM) to about 1 molar (M) in the solution.

D6.2. The method of embodiment D6 or D6.1, wherein the matrix is at a concentration of about 1 milligram per milliliter to about 100 milligrams per milliliter in the solution.

D6.3. The method of any one of embodiments D3 to D6.2, wherein the matrix is at a concentration of about 20 milligrams per milliliter to about 60 milligrams per milliliter in the solution.

D6.4. The method of embodiment D3, wherein the matrix to nanoparticle ratio is about 0.1:1 to about 30,000:1 in the solution.

D6.5. The method of embodiment D6.4, wherein the matrix to nanoparticle ratio is about 1:1 to about 600:1 in the solution.

D6.6. The method of embodiment D6.5, wherein the matrix to nanoparticle ratio is about 13:1 to about 430:1 in the solution.

D7. The method of any one of embodiments D1 to D6, comprising drying the samples on the substrate.

D8. The method of embodiment D7, wherein the drying comprises exposing the samples to a relative humidity of about 30% to about 80%.

D9. The method of embodiment D8, wherein the relative humidity is about 50%.

D10. The method of any one of embodiments D7 to D9, wherein the drying comprises exposing the samples to a temperature of about 15 degrees Celsius to about 35 degrees Celsius.

D11. The method of embodiment D10, wherein the temperature is about 21 degrees Celsius.

D12. The method of any one of embodiments D7 to D11, wherein the drying comprises exposing the samples to an ambient pressure.

D13. The method of any one of embodiments D7 to D12, comprising placing the substrate into a humidity chamber.

D14. The method of any one of embodiments D1 to D13, wherein the samples comprise an analyte.

D15. The method of embodiment D14, wherein the analyte is chosen from nucleotides, oligonucleotides, polynucleotides, nucleic acid, peptides, proteins, polymers (e.g., synthetic polymer, industrial polymer, plastic polymer), saccharides, polysaccharides, sugars, carbohydrates, lectins, lipids, glycoproteins, lipoproteins, small molecules, small chemical entities, metabolites, natural products, pharmaceuticals, conjugates and combinations thereof.

E1. A method for analyzing an analyte by matrix assisted laser desorption ionization (MALDI) mass spectrometry (MS), comprising:
depositing an analyte onto one or more of the samples on a substrate of any one of embodiments A1, A2, B1, B2 and C1 to C52;
volatilizing and ionizing the analyte in one or more of the samples, thereby generating ions; and
analyzing the analyte by MALDI MS.

E1.1. A method for analyzing an analyte by matrix assisted laser desorption ionization (MALDI) mass spectrometry (MS), comprising:
depositing a sample comprising an analyte, matrix and nanoparticles onto one or more domains on a substrate, thereby generating a substrate of any one of embodiments A1, A2, B1, B2 and C1 to C52 comprising analyte in one or more samples;
volatilizing and ionizing the analyte at each of the samples, thereby generating ions; and
analyzing the analyte by MALDI MS.

E2. The method of embodiment E1, wherein the analyte is in solution and the sample that is substantially crystallized or portion thereof dissolves after the analyte is deposited.

E3. The method of embodiment E2, wherein the substrate is exposed to conditions under which the sample that dissolves re-crystallizes.

E4. The method of any one of embodiments E1 to E3, wherein the analyte is chosen from nucleotides, oligonucleotides, polynucleotides, nucleic acid, peptides, proteins, polymers (e.g., synthetic polymer, industrial polymer, plastic polymer), saccharides, polysaccharides, sugars, carbohydrates, lectins, lipids, glycoproteins, lipoproteins, small molecules, small chemical entities, metabolites, natural products, pharmaceuticals, conjugates and combinations thereof.

E5. The method of any one of embodiments E1 to E4, wherein the mass spectrometer is configured to perform MALDI time of flight (MALDI-TOF) MS.

F1. A composition comprising a matrix assisted laser desorption ionization (MALDI) mass spectrometry (MS) matrix and nanoparticles,
which matrix is not covalently linked to the nanoparticles,
which nanoparticles are not in association with a peptide or protein; and
the composition comprises substantially no component or components that react with the matrix or the nanoparticles, or the matrix and the nanoparticles, and covalently link the matrix to the nanoparticles.

F2. The composition of embodiment F1, wherein the matrix is suitable for mass spectrometry analysis of a nucleic acid.

F3. A composition comprising a matrix and nanoparticles, wherein the matrix consists essentially of 3-HPA.

F4. The composition of any one of embodiments F1 to F3, wherein the matrix and the nanoparticles are in solution.

F5. The composition of any one of embodiments F1 to F4, wherein there is substantially no ionic, hydrophobic, hydrogen bond or van der Walls association between the matrix and the nanoparticles, and the composition comprises substantially no component or components that react with the matrix or the nanoparticles, or the matrix and the nanoparticles, and associate the matrix with the nanoparticles by an ionic, hydrophobic, hydrogen bond or van der Walls association.

F6. The composition of embodiment F5, wherein there is substantially no ionic association between the matrix and the nanoparticles.

F7. The composition of any one of embodiment F5, wherein there is substantially no hydrophobic association between the matrix and the nanoparticles.

F8. The composition of any one of embodiment F5, wherein there is substantially no hydrogen bond association between the matrix and the nanoparticles.

F9. The composition of embodiment F5, wherein there is substantially no van der Walls association between the matrix and the nanoparticles.

F10. The composition of any one of embodiments F1 to F9, wherein there is substantially no association between the matrix and the nanoparticles, and the composition comprises substantially no component or components that react with the matrix or the nanoparticles, or the matrix and the nanoparticles, and associate the matrix with the nanoparticles.

F11. The composition of any one of embodiments F1 to F10, wherein the matrix comprises a matrix chosen from 2,5-dihydroxybenzoic acid (DHB) and 3-hydroxypicolinic acid (3-HPA).

F12. The composition of embodiment F11, wherein the matrix comprises 3-HPA.

F13. The composition of any one of embodiments F1 to F12, wherein the matrix consists essentially of a single matrix.

F14. The composition of embodiment F13, wherein the matrix consists essentially of 3-H PA.

F15. The composition of any one of embodiments F1 to F14, wherein the matrix consists essentially of multiple matrix components.

F16. The composition of any one of embodiments F1 to F15, wherein the composition comprises one or more additives.

F17. The composition of embodiment F16, wherein the composition comprises ascorbic acid.

F18. The composition of embodiment F16 or F17, wherein the composition comprises ammonium oxalate.

F19. The composition of any one of embodiments F16 to F18, wherein the composition consists essentially of 3-H PA, ascorbic acid, ammonium oxalate and the nanoparticles.

F20. The composition of any one of embodiments F16 to F19, wherein the nanoparticles are not in covalent association with the one or more additives, and the composition comprises substantially no component or components that react with the one or more additives or the nanoparticles, or the one or more additives and the nanoparticles, and covalently link the one or more additives to the nanoparticles.

F20.1. The composition of any one of embodiments F16 to F19, wherein there is substantially no ionic, hydrophobic, hydrogen bond or van der Walls association between the one or more additives and the nanoparticles, and the composition comprises substantially no component or components that react with the one or more additives or the nanoparticles, or the one or more additives and the nanoparticles, and associate the one or more additives with the nanoparticles by an ionic, hydrophobic, hydrogen bond or van der Walls association.

F21. The composition of any one of embodiments F16 to F19, wherein the nanoparticles are not in association with the one or more additives, and the composition comprises substantially no component or components that react with the one or more additives or the nanoparticles, or the one or more additives and the nanoparticles, and associate the one or more additives with the nanoparticles.

F22. The composition of any one of embodiments F1 to F21, wherein the nanoparticles have an average, mean, median, nominal, minimum or maximum diameter of about 1 nanometer to about 100 nanometers.

F23. The composition of embodiment F22, wherein the nanoparticles have an average, mean, median, nominal, minimum or maximum diameter of about 5 nanometers to about 30 nanometers.

F24. The composition of embodiment F23, wherein the nanoparticles have an average, mean, median, nominal, minimum or maximum diameter of about 10 nanometers to about 20 nanometers.

F25. The composition of embodiment F24, wherein the nanoparticles have an average, mean, median, nominal, minimum or maximum diameter of about 15 nanometers.

F26. The composition of any one of embodiments F1 to F25, wherein the nanoparticles are substantially inert.

F27. The composition of embodiment F26, wherein the nanoparticles are substantially not derivatized with functional chemical groups.

F28. The composition of embodiment F25 or F27, wherein the nanoparticles do not substantially associate with an analyte.

F29. The composition of embodiment F27 or F28, wherein the nanoparticles substantially form no covalent, ionic, hydrophobic, hydrogen bond or van der Walls association with the an analyte.

F30. The composition of embodiment F28 or F29, wherein the analyte is a nucleic acid analyte.

F31. The composition of any one of embodiments F1 to F30, wherein the nanoparticles substantially do not give rise to MALDI MS signals.

F32. The composition of any one of embodiments F1 to F31, wherein the nanoparticles contain substantially no metal.

F33. The composition of any one of embodiments F1 to F33, wherein the nanoparticles comprise, consist essentially of, or consist of one or more metals.

F34. The composition of F31 or F33, wherein the one or more metals are chosen from gold, silver, platinum, aluminum, titanium, tantalum and vanadium.

F35. The composition of F31 or F33, wherein the one or more metals is one metal and the metal is iron.

F36. The composition of any one of embodiments F1 to F35, wherein the nanoparticles do not substantially form multimers.

F37. The composition of any one of embodiments F1 to F36, wherein the nanoparticles comprise $SiO_2$.

F38. The composition of embodiment F37, wherein the nanoparticles are fumed silica particles.

F39. The composition of any one of embodiments F1 to F38, wherein the nanoparticles are at a concentration of about 1 microgram per milliliter to about 500 micrograms per milliliter in the solution.

F40. The composition of embodiment F38, wherein the nanoparticles are at a concentration of about 75 micrograms per milliliter to about 300 micrograms per milliliter in the solution.

F41. The composition of embodiment F39, wherein the nanoparticles are at a concentration of about 125 micrograms per milliliter or about 250 micrograms per milliliter in the solution.

F42. The composition of any one of embodiments F1 to F41, wherein the matrix is at a concentration of about 1 mM to about 1 M.

F43. The composition of any one of embodiments F1 to F41, wherein the matrix is at a concentration of about 1 milligram per milliliter to about 100 milligrams per milliliter.

F44. The composition of embodiment F43, wherein the matrix is at a concentration of about 20 milligrams per milliliter to about 60 milligrams per milliliter.

F45. The composition of any one of embodiments F1 to F44, wherein the matrix to nanoparticle ratio is about 0.1:1 to about 30,000:1.

F46. The composition of embodiment F45, wherein the matrix to nanoparticle ratio is about 1:1 to about 600:1.

F47. The composition of embodiment F46, wherein the matrix to nanoparticle ratio is about 13:1 to about 430:1.

F48. The composition of any one of embodiments F1 to F47, wherein the composition is substantially solid.

F49. The composition of embodiment F48, wherein the composition is substantially crystalline.

G1. A matrix assisted laser desorption ionization (MALDI) mass spectrometry (MS) substrate comprising a substantially planar surface and a plurality of sample containment structures;
   each of which containment structures comprises one or more depressions disposed in the substrate, one or more projections disposed on the substrate, or one or more depressions disposed in the substrate and one or more projections disposed on the substrate; and
   each of which containment structures is configured to isolate a sample comprising a MALDI MS matrix in a particular location of the substrate as a sample dries on the substrate, and is configured to contain the sample after the sample has dried.

G2. The mass spectrometry substrate of any one of embodiments G1 to G3, wherein each of the containment structures comprises one or more edges or points.

G3. The mass spectrometry substrate of embodiment G2, wherein the one or more edges are formed between a surface of the containment structure and the substantially flat substrate surface.

G4. The mass spectrometry substrate of embodiment G2 or G3, wherein the one or more edges are formed between two surfaces of the containment structure.

G5. The mass spectrometry substrate of any one of embodiments G1 to G4, wherein each of the containment structures comprises a substantially flat surface or a substantially curved surface, or a substantially flat surface and a substantially curved surface.

G6. The mass spectrometry substrate of any one of embodiments G1 to G5, wherein each of the containment structures is chosen from wells, ridges and posts.

G7. The mass spectrometry substrate of embodiment G6, comprising wells.

G8. The mass spectrometry substrate of embodiment G7, wherein the profile of the wells comprises a rectangle, polygon, triangle, circle, oval or ellipse.

G9. The mass spectrometry substrate of embodiment G7 or G8, wherein the wells have a width at the substrate surface of about 2 millimeters or less and have a depth of about 100 micrometers or less.

G10. The mass spectrometry substrate of any one of embodiments G7 to G9, wherein a wall of the wells comprise a substantially curved surface or a substantially flat surface, or a substantially curved surface and a substantially flat surface.

G11. The mass spectrometry substrate of any one of embodiments G7 to G10, wherein the bottom of each of the wells comprises a substantially curved surface or a substantially flat surface, or a substantially curved surface and a substantially flat surface.

G12. The mass spectrometry substrate of embodiment G6, which comprises ridges or posts.

G13. The mass spectrometry substrate of embodiment G13, wherein the ridges are in a containment structure that comprises a well.

G14. The mass spectrometry substrate of embodiment G14, wherein each of the wells are raised wells.

G15. The mass spectrometry substrate of embodiment G14, wherein the wells have an internal width at the proximal opening of each well of about 2 millimeters or less and have a depth of about 100 micrometers or less.

G16. The mass spectrometry substrate of embodiment G14 or G15, wherein a wall of each of the wells comprises a substantially curved surface or a substantially flat surface, or a substantially curved surface and a substantially flat surface.

G17. The mass spectrometry substrate of any one of embodiments G14 to G16, wherein the bottom of each of the wells comprises a substantially curved surface or a substantially flat surface, or a substantially curved surface and a substantially flat surface.

G18. The mass spectrometry substrate of any one of embodiments G1 to G17, wherein the structures are disposed on the substrate in an array.

G19. The mass spectrometry substrate of embodiment G18, comprising about 24 structures.

G20. The mass spectrometry substrate of embodiment G18, comprising about 96 structures.

G21. The mass spectrometry substrate of embodiment G18, comprising about 384 structures.

G22. The mass spectrometry substrate of any one of embodiments G1 to G21, wherein the substrate comprises one or more surfaces that are substantially hydrophobic.

G23. The mass spectrometry substrate of any one of embodiments G1 to G22, wherein the containment structures comprise one or more surfaces that are substantially hydrophobic.

G24. The mass spectrometry substrate of embodiment G22 or G23, wherein the substrate comprises one or more surfaces that are relatively hydrophilic.

G25. The mass spectrometry substrate of any one of embodiments G22 to G24, wherein the containment structures comprise one or more surfaces that are relatively hydrophilic.

G26. The mass spectrometry substrate of embodiment G24 or G25, wherein the one or more surfaces that are relatively hydrophilic comprise a photoresist.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the technology. Although the technology has been described in substantial detail with reference to one or more specific embodiments, those of ordinary skill in the art will recognize that changes may be made to the embodiments specifically disclosed in this application, yet these modifications and improvements are within the scope and spirit of the technology.

The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. Further, when a listing of values is described herein (e.g., about 50%, 60%, 70%, 80%, 85% or 86%) the listing includes all intermediate and fractional values thereof (e.g., 54%, 85.4%). Thus, it should be understood that although the present technology has been specifically disclosed by representative embodiments and optional features, modification and variation of the concepts herein disclosed may be resorted to by those skilled in the art, and such modifications and variations are considered within the scope of this technology.

Certain embodiments of the technology are set forth in the claim(s) that follow(s).

What is claimed is:

1. A matrix assisted laser desorption ionization (MALDI) mass spectrometry (MS) substrate comprising: a plurality of samples, which samples comprise nanoparticles and a MALDI MS matrix,
which samples are substantially uniformly crystalized,
which nanoparticles are inert and which matrix is not covalently linked to the nanoparticles,
wherein there is substantially no ionic association between the matrix and the nanoparticles,
wherein the mole ratio or molar concentration ratio of the amount of matrix to the amount of nanoparticles is about 10:1 to about 20,000:1, and
which nanoparticles are not in association with a peptide or protein.

2. The substrate of claim 1, comprising a substantially planar surface and a plurality of sample containment structures;
each of which containment structures comprises one or more depressions disposed in the substrate, one or more projections disposed on the substrate, or one or more depressions disposed in the substrate and one or more projections disposed on the substrate; and
each of which containment structures is configured to isolate a sample comprising the matrix in a particular location of the substrate as a sample dries on the substrate, and is configured to contain the sample after the sample has dried.

3. The substrate of claim 1, wherein the matrix is suitable for mass spectrometry analysis of a nucleic acid.

4. The substrate of claim 1, wherein one or more of the samples comprise an analyte.

5. The substrate of claim 4, wherein the analyte is chosen from a nucleotide, an oligonucleotide, a polynucleotide, a nucleic acid, a peptide, a protein, a polymer, a saccharide, a polysaccharide, a sugar, a carbohydrate, a lectin, a lipid, a glycoprotein, a lipoprotein, a small molecule, a small chemical entity, a metabolite, a natural product, a pharmaceutical, a conjugate and a combination thereof.

6. The substrate of claim 1, wherein one or more of the samples comprise 3-HPA.

7. The substrate of claim 1, wherein one or more of the samples comprise ascorbic acid.

8. The substrate of claim 7, wherein each of the samples consists essentially of 3-HPA, ascorbic acid, ammonium oxalate and the nanoparticles, and optionally an analyte.

9. The substrate of claim 1, wherein the nanoparticles comprise $SiO_2$.

10. The substrate of claim 1, comprising a silicon chip.

11. The substrate of claim 1, wherein there is substantially no hydrophobic association between the matrix and the nanoparticles.

12. The substrate of claim 1, wherein there is substantially no hydrogen bond association between the matrix and the nanoparticles.

13. The substrate of claim 1, wherein the size of the nanoparticles is about 10 nm to about 20 nm.

14. The substrate of claim 1, wherein the size of the nanoparticles is about 15 nm.

15. The substrate of claim 1, wherein the size of the nanoparticles is about 5 nm to about 30 nm.

16. The substrate of claim 1, wherein the mole ratio or molar concentration ratio of the amount of matrix to the amount of nanoparticles is about 1000:1, 900:1, 800:1, 700:1, 600:1, 500:1, 400:1, 350:1, 330:1, 300:1, 250:1, 225:1, 200:1, 175:1, 150:1, 125:1 or 100:1.

17. The substrate of claim 16, wherein the mole ratio or molar concentration ratio of the amount of matrix to the amount of nanoparticles is about 300:1.

18. The substrate of claim 16, wherein the mole ratio or molar concentration ratio of the amount of matrix to the amount of nanoparticles is about 250:1.

19. The substrate of claim 16, wherein the mole ratio or molar concentration ratio of the amount of matrix to the amount of nanoparticles is about 225:1.

* * * * *